United States Patent [19]

Birnbaum

[11] 4,254,145

[45] Mar. 3, 1981

[54] TOPICAL APPLICATION OF PROSTAGLANDIN HYPOTENSIVE AGENTS

[75] Inventor: Jay E. Birnbaum, Pomona, N.Y.

[73] Assignee: American Cyanamid Company, Stamford, Conn.

[21] Appl. No.: 934,199

[22] Filed: Aug. 16, 1978

[51] Int. Cl.$^3$ ................ A61K 31/22; A61K 31/215
[52] U.S. Cl. ........................... 424/305; 424/311; 424/317; 424/318; 424/331; 424/337; 424/339; 424/343
[58] Field of Search ................. 424/305, 317, 331

[56] References Cited

U.S. PATENT DOCUMENTS

| | | | |
|---|---|---|---|
| 3,551,554 | 8/1968 | Herschler | 424/7 |
| 4,061,670 | 7/1976 | Floyd et al. | 424/305 X |
| 4,078,083 | 3/1978 | Babej et al. | 424/317 |
| 4,080,506 | 3/1978 | Morozowich | 424/317 |
| 4,094,899 | 6/1978 | Hess | 424/317 |
| 4,103,026 | 7/1978 | Carlson | 424/305 |

OTHER PUBLICATIONS

Williams et al., Chemical Abstracts 88:183486x (1978).

*Primary Examiner*—Leonard Schenkman
*Attorney, Agent, or Firm*—Richard J. Hammond

[57] ABSTRACT

Pharmaceutical compositions useful as vasodilators whose activity may be restricted to the site of application by control of the dose applied which comprises a prostaglandin selected from the group consisting of the natural and synthetic analogs of the PGE, PGA and PGE$_\beta$ types in a pharmaceutical carrier. The compositions are applied topically and by local injection to increase peripheral circulation, or to treat peripheral vascular disorders of the arteriospastic and occlusive types. The prostaglandins and pharmaceutical compositions containing them disclosed herein are also administered topically and by local injection to lower the systemic blood pressure of man and warm blooded animals. Systemic action is obtained by the use of an effective dosage greater than that used to induce localized action at the site of application.

74 Claims, 5 Drawing Figures

TOPICAL APPLICATION OF PROSTAGLANDIN HYPOTENSIVE AGENTS

DESCRIPTION OF THE PRIOR ART

Peripheral vascular diseases include a variety of arteriospastic and occlusive disorders. The major difficulty associated with the treatment of such diseases with systemic vasodilators is the inability of these drugs to produce a specific vasodilation in critical ischemic areas. The generalized vasodilation induced by systemic vasodilators may actually exacerbate the ischemia produced by a peripheral vascular disease by shunting the blood into non-ischemic areas.

Non-specificity of activity is also responsible for the numerous side-effects associated with prior art peripheral vasodilators. For example, central sympathetic inhibitors such as reserpine and methyl dopa cause bradycardia, nasal congestion, impotence, depression, drug fever, and hepatic disfunction; $\alpha$-adrenergic receptor blocking agents such as tolazoline, azapetine and phenoxybenzamine cause nasal congestion, aggravation of angina, hypotension, headache and tachycardia; $\beta$-adrenergic stimulating agents such as nylidrin and isoxsuprine cause anxiety, palpitations, aggravation of angina and tachycardia; while direct smooth muscle relaxants such as ethanol, papaverine and cyclandelate cause intoxication, respiratory depression, exacerbation of peptic ulcer, nausea, dizziness and headache.

The potent vasodilator activity of the E-type prostaglandins is well recognized. See, e.g. Bergstrom, S. et. al., The Prostaglandins: A Family of Biologically Active Lipids, *Pharm. Rev.* 20: 1–48, 1968. The systemic administration of the PGE type prostaglandins however, is associated with untoward side effects on many organ systems, while intradermal injection elicits an erythematous response with swelling, hyperalgia and at higher dosages, wheal and flare. U.S. Pat. No. 4,009,282 discloses the use of the PGE series of prostaglandins and their esters to treat proliferating skin diseases.

It has been recently reported that 15(S)-15-methyl $PGE_2$ methyl ester induces an erythema upon topical administration to the skin of a hairless mouse, while $PGE_2$ itself was ineffective in illiciting such a response. See, Lowe, N. J. and Stoughton, R. B., Effects of Topical Prostaglandin $E_2$ Analog on Normal Hairless Mouse Epidermal DNA Synthesis, *The Journal of Investigative Dermatology* 68: 134–137, 1977. Although Lowe and Stoughton disclose the administration of 15(S)-15-methyl $PGE_2$ methyl ester to topically induce an erythema, they do not disclose a method of employing topical formulations of this prostaglandin for a therapeutic purpose, such as for the treatment of peripheral vascular disorders. Nor do they disclose a method of producing cutaneous, vasodilation without associated inflammatory changes.

The anti-hypertensive activity of the natural prostaglandins is well recognized. However, they lack oral efficacy and have a short duration of activity even when administered parenterally, presumably due to the rapid metabolism of the drug. The topical administration of the prostaglandins and antihypertensive formulations of the instant inventions may have a longer duration of activity than the natural prostaglandins administered orally or parenterally.

BRIEF DESCRIPTION OF THE INVENTION

It is an object of the present invention to provide vasodilators for application topically or by local injection free of the difficulties associated with the administration of prior art systemic vasodilators discussed above. More specifically, it is an object of the present invention to provide vasodilators for topical administration or by local injection where activity may be controlled and restricted to the site of administration. Another object of this invention is to provide a method of producing cutaneous vasodilation without associated inflammatory changes.

It is a further object of the present invention to provide a method of lowering the systemic blood pressure of man and other warm blooded animals through topical or other localized administration of prostaglandins of the natural PGE, PGA and $PGF_\beta$ types, or the synthetic analogs of the PGE, PGA and $PGF_\beta$ types.

In accordance with these and other objectives, the present invention provides a pharmaceutical composition for use as a vasodilator whose activity is restricted to its site of administration, which comprises a prostaglandin selected from the group consisting of the natural PGE, PGA and $PGF_\beta$ types and the synthetic analogs of the PGE, PGA, and $PGF_\beta$ types in a pharmaceutical carrier.

In a preferred embodiment of the pharmaceutical compositions of the instant invention, the synthetic prostaglandin is 15-deoxy-16-hydroxy-16-vinyl-$PGE_2$ or its methyl ester in a pharmaceutical carrier, e.g., 10% ethanol in Aquatain® or petrolatum, in an effective concentration, e.g., about 0.16% by W/W prostaglandin in the carrier.

The present invention also provides a method of lowering the systemic blood pressure of man and warm blooded animals which comprises the topical administration of an effective dosage of a prostaglandin selected from the group consisting of the natural or synthetic analogs of the PGE, PGA or $PGF_\beta$ types.

The present invention further provides a method for the treatment of hypertension which comprises applying topically to a mammal suffering from hypertension an amount of a prostaglandin effective to reduce the blood pressure of the mammal.

DETAILED DESCRIPTION OF THE INVENTION

Figure 1:
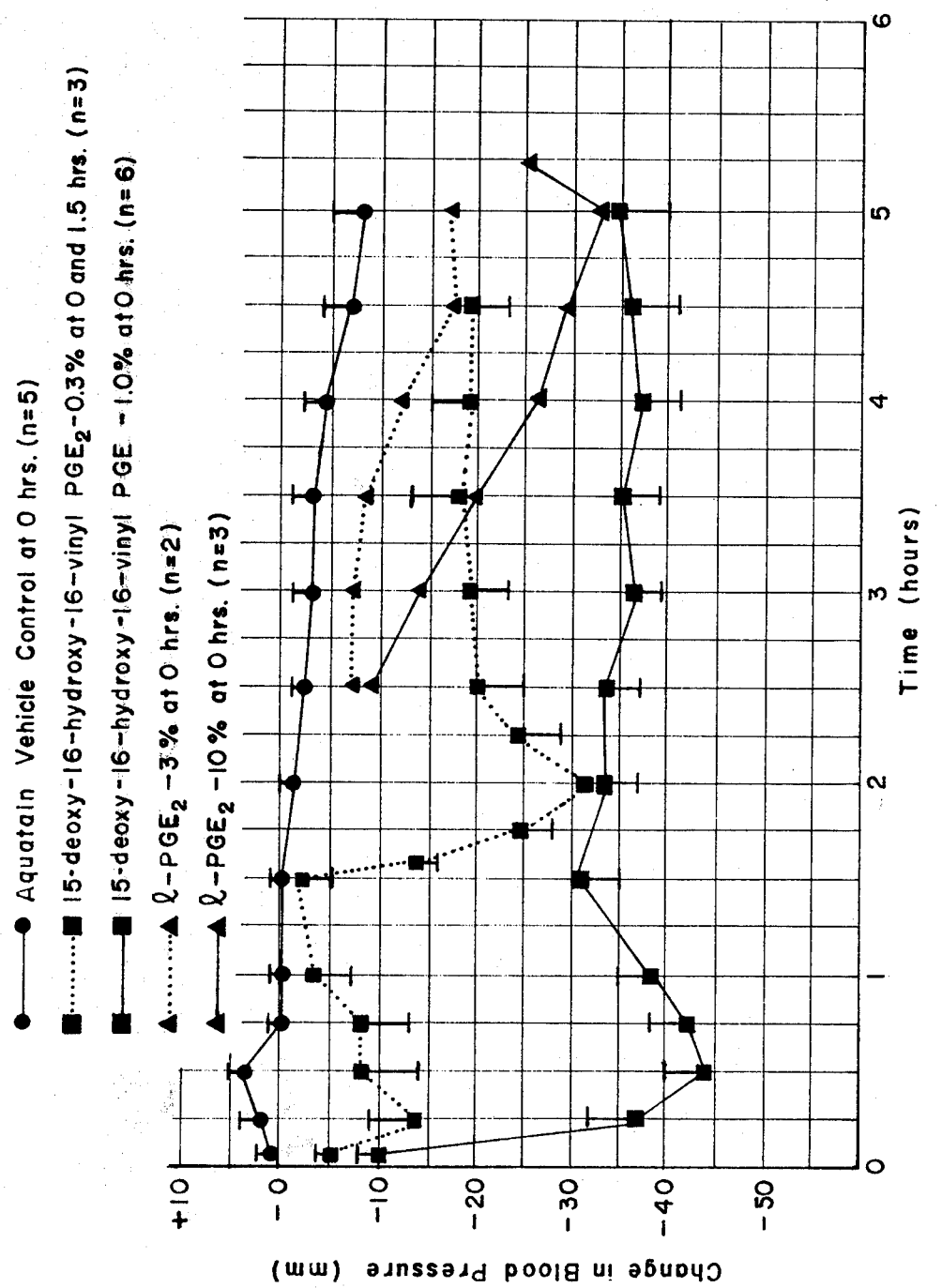

This invention relates to compounds and pharmaceutical preparations which when applied topically or by injection produce a distinct increase in peripheral (cutaneous and deep vessel) circulation. The intense and persistent vasodilation induced by the administration to the skin, of the prostaglandins of the natural or synthetic analogs of the PGE, PGA and $PGE_\beta$ prostaglandin types renders these compounds especially useful for the treatment of peripheral vascular diseases of the arteriospastic and occlusive types. Thus, the prostaglandin compounds and compositions containing them disclosed herein are useful for the treatment of diseases such as Raynaud's phenomenon, Raynaud's disease, Buerger's disease, livedo retcularis, acrocyanosis atherosclerosis, frostbite, vitiligo, alopecia areata, impending gangrene, and other ischemic disorders. Moreover, the ability of the prostaglandins of the instant invention to increase peripheral circulation renders them useful to enhance the rate of healing of wounds, ulcers, infections and proliferative and inflammatory skin lesions including atopic dermatitis, acne and psoriasis; to treat impotency; or to enhance the rate of absorption of pharmaceutically active agents. In addition, topical preparations containing the active prostaglandins of the instant invention may be employed to improve skin color and to promote blush. This invention is also directed to the treatment of hypertension by topical application, particularly by applying the prostaglandins in a pharmaceutical vehicle, or from a sustained release system.

The prostaglandins utilized herein are the natural or synthetic analogs of the PGE, PGA and PGF$_\beta$ prostaglandin types which may be represented by the following general formula:

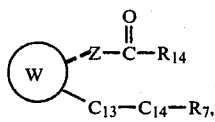

the mirror image thereof, and the racemic mixture thereof wherein W is selected from the group consisting of:

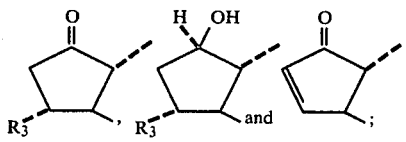

wherein $R_3$ is selected from the group consisting of hydrogen, hydroxyl and $HOCH_2CH_2S-$; Z is selected from the group comprising

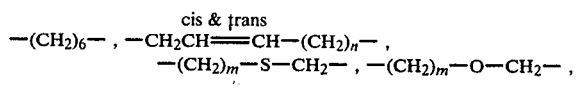

wherein n and m have the value of from 3 to 5 inclusive; $R_{14}$ is selected from the group consisting of hydroxyl, $C_1-C_6$ alkoxy, $-CH_2OH$ or $-CH_2OR_{15}$ wherein $R_{15}$ is $C_2-C_6$ alkanoyl, $C_{13}-C_{14}$ is ethylene or trans-vinylene; $R_7$ is a moiety selected from the group consisting of:

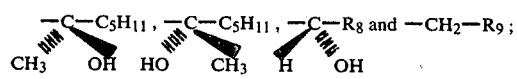

wherein $R_8$ is selected from the group consisting of $C_4-C_7$ alkyl, $C_5H_{11}$, cyclohexyl, cyclopentyl,

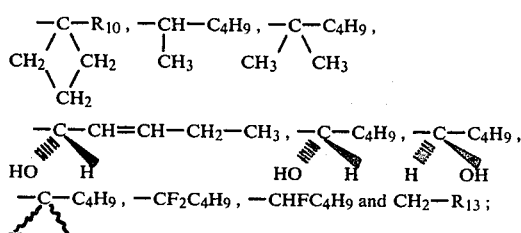

wherein $R_9$ is selected from the group of $C_5H_{11}$,

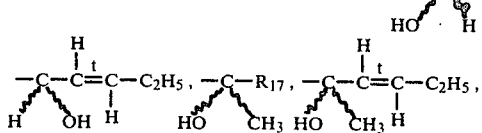

-continued

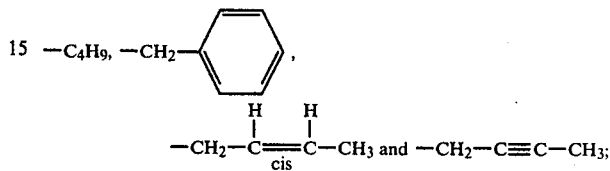

wherein $R_{16}$ is E-1-propenyl, Z-1-propenyl, and $R_{17}$ is $C_3-C_7$ alkyl; $R_{10}$ is selected from the group consisting of $-C_4H_9$, $-CH_2-$⌬ , $-CH_2-\overset{H}{\underset{cis}{C}}=\overset{H}{C}-CH_3$ and $-CH_2-C\equiv C-CH_3$;

and $R_{13}$ is selected from the group consisting of phenyl, benzyl, phenoxy and phenoxy substituted by fluoro, chloro, trifluoromethyl or methyl, and when $R_{14}$ is hydroxy, the pharmacologically acceptable cationic salts thereof. Compounds of the above formula wherein n is 3 and m is 4 are preferred.

A preferred class of compounds are the 15-deoxy-16-hydroxy-substituted prostanoic acids. The ring systems of these compounds are classified in accordance with the conventional prostaglandin types as follows:

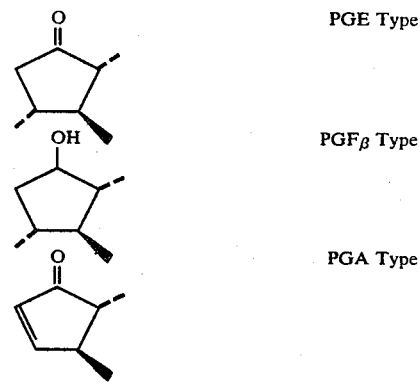

Synthetic analogs of the 16-hydroxy-16-substituted-PGE, PGF$_\beta$ and PGA types are represented by the following general formula and mirror image thereof:

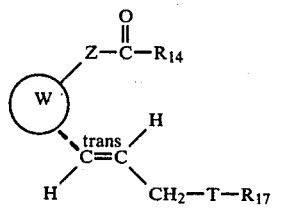

wherein W, Z, $R_{14}$, and $R_{17}$ are as hereinabove defined and T is the divalent radical:

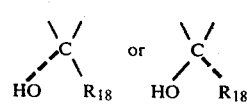

wherein $R_{18}$ is selected from the group comprising hydrogen, methyl, vinyl, methylvinyl, ethynyl and cyclopropyl. Compounds of the above formula wherein n is 3 and m is 4 are preferred.

16-hydroxy-16-substituted synthetic prostaglandin analogs are described in U.S. Pat. No. 4,061,670 which is incorporated by reference. This patent also discloses that 16-hydroxy-16-substituted prostaglandin analogs are useful as hypotensive agents.

Synthetic prostaglandin derivatives of the 1-hydroxymethyl-1-oxo type are described in U.S. application Ser. No. 858,487 (filed Dec. 8, 1977) which is incorporated by reference. This application discloses that the 1-hydroxymethyl-1-oxo-prostane derivatives of the $E_1$ series disclosed therein are useful as topical vasodilators and as hypotensive agents.

Compounds employed by this invention are also described by U.S. Pat. No. 4,028,396, U.S. patent application Ser. No. 782,797, filed Mar. 30, 1977; Ser. Nos. 782,853 and 782,852, filed Mar. 30, 1977; Ser. Nos. 857,848, 857,849 and 857,714, filed Dec. 5, 1977; Ser. Nos. 858,589, 858,487, 858,588, 858,504, 858,580 and 858,579, filed Dec. 8, 1977; which are incorporated by reference.

A 15-deoxy-16-hydroxy-16-substituted prostaglandin may consist of two dl racemates (16α-hydroxyl and 16β-hydroxyl) which, on occasion, are separable into the 16α and 16β epimers. A species claim wherein the stereochemistry of the $C_{16}$ carbon is not specified encompasses the optically active 16α and 16β forms of the compound and the racemic mixtures thereof.

Useful pharmacologically acceptable salts of the above-described synthetic prostaglandins when $R_{14}$ is hydroxyl are those with pharmacologically acceptable metal cations, ammonium, amine cations or quaternary ammonium cations.

Preferred metal cations are those derived from the alkali metals, e.g., lithium, sodium and potassium, and from the alkaline earth metals, e.g., magnesium and calcium, although cationic forms of other metals, e.g., aluminum, zinc and iron, are within the scope of the invention.

Pharmacologically acceptable amine cations are those derived from primary, secondary or teritary amines such as mono-, di- or triisopropylamine, N-methylhexylamine, decylamine, dodecylamine, allylamine, crotylamine, cyclopentylamine, dicyclohexylamine, allylamine, crotylamine, cyclopentylamine, dicyclohexylamine, mono- or dibenzylamine, α- or β-phenylethylamine, ethylenediamine, diethylenetriamine, and arylaliphatic amines containing up to and including 18 carbon atoms, as well as heterocyclic amines, e.g., piperidine, morpholine, pyrrolidine, piperazine and lower alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, or triethanolamine, ethyldiethanolamine, N-butylethanolamine, 2-amino-2-methyl-1-propanol, tris(hydroxymethyl)-aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharamacologically acceptable quarternary ammonium cations are tetramethylammonium, tetraethylammonium, benzyltrimethylammonium, phenyltriethylammonium and the like.

The prostaglandins of the instant invention, when applied to the skin topically, or by injection intradermally, or intra- or peri-lesionally induce an intense and persistant vasocilation which is restricted to the site of application when used in limited amounts. Since the activity of the prostaglandins of the instant invention when administered either topically or by local injection is restricted to the site of application, the use of these compounds for the treatment of peripheral vascular diseases is preferable to the use of systemically active drugs disclosed by the prior art which are unable to produce a specific vasodilation in the critical arteriospastic or ischemic area. The compositions of this invention may also enhance blood flow and may be employed to treat disorders where an enhanced blood flow is beneficial.

The term topical as employed herein, relates to the use of the prostaglandin vasodilator in a suitable carrier or drug delivery system, and applied at the site of the disease for the exertion of local action. Conventional pharmaceutical forms which may be employed as carriers for the active prostaglandins include ointments, creams, lotions, pastes, jellies, sprays, aerosols, bath oils, or other pharmaceutical carriers which accomplish direct contact between the prostaglandin and the surface of the skin area to be treated. The term "ointment" as employed herein, comprises formulations (including creams) having oleaginous, absorptive, water-insoluable, and emulsion-type bases, or viscous fluids generally which are capable of providing prolonged contact between the skin surface and the prostaglandin contained in the carrier. For example, petrolatum, lanolin, polyethylene glycols, soaps, waxes, as well as mixtures thereof. In some cases it may be necessary to dissolve the prostaglandin in an appropriate solvent such as ethanol, DMSO (dimethylsulfoxide), polyethylene glycol, and the like to facilitate incorporation into a pharmaceutical preparation, and the term "ointment" is intended to include carriers containing such solubilizing agents.

A preferred ointment carrier is white petrolatum which may be employed in combination with antioxidants such as mixed tocopherols to enhance the shelf-life and stability of the formulation. Moreover, the ointment may also employ viscosity modifiers such as paraffin wax, lanolin wax or other compatable solid waxes to adjust the viscosity of the formulation as desired. A preferred topical formulation of 15-deoxy-16-hydroxy-16-vinyl-PGE$_2$ or its methyl ester comprises by W/W, from about 75 to 95% white petrolatum, 5 to 25% of a solubilizer such as diisopropyl adipate or polyethylene glycol (PEG) 2000 dioleate, and 0.01 to 2% of the prostaglandin. As an alternative to employing white petrolatum, a carrier consisting of mineral oil and high molecular weight polyethylene waxes, such as Plastibase ® may be employed.

A concentration-response relationship has been noted for the topical preparations of the instant invention; that is, as the concentration of the prostaglandin in a given topical formulation is increased, for the same amount of the preparation administered, to the same total area of skin, the resultant vasodilation is intensified. Thus, the concentration of the active prostaglandin in the carrier, or the amount of the preparation applied may be adjusted to induce a localized vasodilation of the desired intensity. Moreover, the choice of a particular carrier may augment the activity of a given prostaglandin relative to the activity of that compound in other carriers. For example, the solution of 15-deoxy-16-hydroxy-16-vinyl-PGE$_2$ in Aquatain ® base is clearly augmented, relative to solutions of the same synthetic prostaglandin analog in either an ethanol or DMSO solution.

The prostaglandins of the instant invention when topically applied may induce a persistent and distinct erythema at varying dosages, however, some prostaglandins produce a more intense and persistent erythema than others. The amount of the pharmaceutical preparation administered to produce a localized vasodilation of the desired degree will vary depending upon the particular prostaglandin employed, the area of the body to which the drug is administered, as well as the individual characteristics of the subject treated. In general, however, the pharmaceutical preparations for topical administration contain from about 0.001% to about 10%, and preferably from about 0.01 to 5% by W/W of the active prostaglandin in a suitable carrier. For example, 0.25% of 15-deoxy-16-hydroxy-16-vinyl-PGE$_2$ in a 10% ethanol in Aquatain ® or petrolatum formulation. This may represent a dosage of about 0.01 to 10 mg/m$^2$ for the more active prostaglandins.

The localized administration of the effective prostaglandin may also be accomplished by injection. Injection refers to positioning a pharmaceutical prepartion suitable for parenteral administration in the high dermis by needle or by high pressure air injection. The injectable compositions of the instant invention may also be administered intra- or peri-lesionally; that is by injection into the lesion or into the tissue immediately surrounding the lesion.

For administration by injection, fluid forms are prepared utilizing the active compound and a sterile vehicle, water being preferred when the composition is to be used immediately, i.e., not stored. The compound, depending on the form and concentration used, can be either suspended or dissolved in the vehicle. In preparing solutions, a water soluble form of the compound can be dissolved in water for injection and filter sterilized before transferring the solution into a suitable vial or ampule. Advantageously, adjuvants such as a local anesthetic, preservative and buffering agents can be dissolved in the vehicle. To enhance stability, the composition can be frozen within the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved, and sterilization cannot be accomplished by filtration. The compound can be sterilized before suspension in the sterile vehicle.

The effective dosage administered by injection at one or more sites to produce a localized or regional increase in circulation or to treat an ischemic area associated with a peripheral vascular disease comprises from about 0.001 to about 10 mg of the prostaglandin and preferably from about 0.003 to 2 mg per day. For the more active prostaglandins, however, such as 15-deoxy-16-hydroxy-16-vinyl-PGE$_2$ parenteral administrations of from about 0.002 to 0.2 mg per day constitutes an effective dosage. The degree to which the resultant effect is localized or generalized is determined by the amount and activity of the prostaglandin, and the number and distribution of injection sites.

Injectable compositions are prepared containing the prostaglandin in a pharmaceutical carrier suitable for parenteral administration in a concentration of from about 0.001 to 5%.

In addition to the utility of the prostaglandins of this invention as vasodilators, the administration of the prostaglandin topically (including sublingually or buccally) or by local injection results in a distinct reduction in the systemic blood pressure. Moreover, the topical administration of the natural and synthetic prostaglandins of this invention results in a longer duration of activity than is observed upon the oral or parenteral administration of the natural prostaglandins known to possess antihypertensive activity.

For topical hypotensive applications, the prostaglandins is administered in single or multiple doses of about 0.1 mg to 10 mg per kg, preferably from about 0.4 mg to 4 mg per kg of body weight total, per day. For the more active prostaglandins such as 15-deoxy-16-hydroxy-16-vinyl-PGE$_2$ and its methyl ester, however, an effective topical dosage may comprise from about 0.1 to 4 mg per kg of body weight per day.

An effective dosage of the active prostaglandin may be dissolved in a pharmaceutical carrier suitable for topical administration and applied directly to the skin. The preferred carrier for topical administration is petrolatum or a 10% ethanol (or other solvent material) in Aquatain ®, or other pharmaceutical cream based on waxes, soaps or emmolients. The preferred prostaglandin is 15-deoxy-16-hydroxy-16-vinyl-PGE$_2$ or its methyl ester. When a high dosage of the prostaglandin is administered, the total amount of preparation administered may be adjusted by employing a preparation more highly concentrated in the prostaglandin.

Preferably topical preparations comprise from about 0.3 to 20% by W/W, most preferably from 1% to 5% by W/W of the prostaglandin. The topical formulations described above with regard to vasodilator applications, modified to contain an effective concentration of the prostaglandin may be employed for hypotensive applications. The prostaglandin may also be topically applied in solutions, such as alcoholic, i.e., ethanolic solutions of the prostaglandin.

Alternatively, the prostaglandin may be topically administered through the medium of a drug delivery system. A drug delivery bandage of the type described below, capable of continuously administering a metered amount of the prostaglandin over a prolonged period of time i.e., 24 hours, may be employed for this purpose. Thus, a continuous reduction in systemic blood pressure over a 24-hour period may be accomplished by the application of a drug delivery bandage to the skin containing a 24-hour dosage of the prostaglandin either alone or in solution.

Suitable drug delivery systems of the bandage-type comprise a drug reservoir disposed between a backing member and a pressure sensitive adhesive layer. The wall of the reservoir adjoining the adhesive layer, and the adhesive layer are permeable to the drug.

In use, the bandage is applied to the skin so that the adhesive layer forms a tight seal between the skin and the bandage. The prostaglandin within the drug reservoir, migrates through the reservoir wall which acts as a solubility membrane, and into the adhesive layer by diffusion when the drug is soluble in the reservoir wall. Since the adhesive layer is in contact with the skin, drug molecules which are continuously removed from the outer surface of the reservoir wall, migrate through the adhesive layer and are absorbed by the skin.

Both the thickness and composition of the reservoir wall-solubility membrane may be adjusted to allow for the metered control of drug release over a prolonged period of time. The reservoir walls may be formed of, for example, the organopolysiloxane rubbers, or the hydrophilic polymers of monoesters of an olefinic acid, such as acrylic and methacrylic acid. The pressure sensitive adhesive may be formed of any known dermatologically acceptable adhesive which permits drug migration, for example: acrylic resins such as polymers of esters of acrylic acid with alcohols such as n-butanol, pentanol, isopentanol, 2-methyl-butanol, 1-methyl-butanol, 1-methyl-pentanol, 2-methyl-pentanol, 3-methyl-pentanol, 2-ethylbutanol, isooctanol, n-decanol, or n-dodecanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert.-butylacrylamide, itaconic acid, vinylacetate, N-branced alkyl maleamic acids wherein the alkyl group has 10 to 24 carbon atoms, glycol diacrylates, or mixtures of these; elastomeric silicone polymers; polyurethane elastomers; rubbery polymers, such as polyisobutylene, polyisoprene, polybutadiene; vinyl polymers, such as polyvinylalcohol, polyvinylpyrrolidone, and polyvinylacetate; cellulose derivatives such as ethyl cellulose, methyl cellulose, and carboxymethyl cellulose; natural gums such as guar, acacia, pectins, etc. Thus, a 24-hour topical dosage of the prostaglandin alone, or in a suitable solvent may be contained by the reservoir and administered in metered amounts by the drug-delivery bandage over a 24-hour period.

The drug delivery system may also comprise a backing member carrying a pressure-sensitive adhesive through which permeable microcapsules containing the topically active prostaglandin or a solution thereof are distributed. In use, the bandage is applied to the skin, so that the adhesive layer forms a tight seal between the skin and the bandage, the drug migrates from within the microcapsules which act as solubility membranes and into the adhesive layer by diffusion. When the drug reaches the outer surface of the adhesive layer it is absorbed by the skin. Any of the well-known dermatologically acceptable pressure-sensitive adhesives, enumerated above which permit drug migration may be employed.

Preferred encapsulating materials are the silicon rubbers especially dimethylpolysiloxane, hydrophilic acrylate or methacrylate polymers, polyvinyl acetate, plasticized PVC, plasticized nylon, collagen, gelatin and waxes. The encapsulating material can be uniformly impregnated with the drug or may act as a thin coating around the prostaglandin solution to form micro-capsules having interior chambers containing the drug. Alternatively, particles of matrix materials such as starch, gum acacia, gum tragacanth or polyvinylchloride can be impregnated with the solution and encapsulated with one of the other encapsulating materials. The use of matrix and encapsulating membranes of different materials may be employed to slow the rate of release of the prostaglandin.

In each of the above-described bandage-type drug delivery systems, the prostaglandin may be dissolved in an absorable pharmacologically acceptable solvent to facilitate the passage of the prostaglandin through the permeable membranes of the bandage and, its absorption by the skin. Such solvents include DMSO; alcohols containing 2 to 10 carbon atoms, such as hexanol, cyclohexanol, benzylalcohol, 1,2-butanediol, glycerol, and amyl alcohol; hydrocarbons having 5 to 12 carbon atoms such as n-hexane, cyclohexane, and ethyl benzene; aldehydes and ketones having 4 to 10 carbon atoms such as heptyl aldehyde, cyclohexanone, and benzaldehyde; esters having 4 to 10 carbon atoms such as amyl acetate and benzyl propionate; ethereal oils such as oil of eucalptus, oil of rue, cumin oil, limonene, thymol, and 1-pinene; halogenated hydrocarbons having two to eight carbon atoms such as n-hexyl chloride, n-hexyl bromide, and cyclohexyl chlorides, or mixtures of any of the foregoing solvents.

Examples of suitable bandage-type drug delivery systems of the type described above are disclosed in U.S. Pat. Nos. 3,598,122, 3,598,123 and 4,031,894 which are incorporated by reference. Although these systems are particularly useful for topical applications of the prostaglandin for systemic blood pressure lowering, they may also be employed to administer the prostaglandin in appropriate dosages to induce a localized vasodilation.

The following examples describe the manner and process of making and using the invention, but are not to be construed as a limitation thereon.

EXAMPLE I

Effects of Topically Applied Cream Preparations of All Racemic 15-Deoxy-16-Hydroxy-16-Vinyl $PGE_2$ and l-$PGE_2$ on the Mean Arterial Blood Pressure of Spontaneously Hpertensive Rats Spontaneously hypertensive male rats (Taconic Farms) weighing 275–300 grams were shaved and depilated on the abdomen the evening before testing, with a standard mixture of barium sulfide and gum acacia. Rats were fasted overnight and allowed water ad libitum. On the day of testing all racemic 15-deoxy-16-hydroxy-16-vinyl-$PGE_2$ and l-$PGE_2$ were dissolved in ethanol. Aliquots of 0.1 ml of solutions of appropriate concentrations were added to 0.9 g Aquatain ® base to yield preparations of approximately 0.3% and 1.0%, 15-deoxy-16-hydroxy-16-vinyl-$PGE_2$ and 3% and 10% $PGE_2$ by W/W of the active prostaglandin. Vehicle control was prepared by mixing 0.1 ml ethanol in 0.9 g Aquatain ®. Rats were restrained in a supine position on a board. Lidocain (2%) was injected subcutaneously in the femoral area. The iliac artery was exposed and entered with a 26 gauge needle to monitor blood pressure. After an equilibration period the blood pressure was recorded continuously on a multichannel physiograph. Aquatain ® preparations of the prostaglandins were applied to a circular area of approximately 3.5 cm diameter on the abdomen by means of a cotton applicator stick (one swab), so as to apply approximately 24 mg of the preparation.

The effects of 15-deoxy-16-hydroxy-16-vinyl-$PGE_2$ and l-$PGE_2$ on the mean arterial blood pressure of spontaneously hypertensive rats recorded over a 5-hour period was summarized in FIG. 1. 15-Deoxy-16-vinyl-$PGE_2$, 3% formulation was applied at 0 hours and 1.5 hours, all other formulations were applied at 0 hours. The reference in FIG. 1 refers to the number of rats tested.

EXAMPLE 2

Effects of Topically Applied Ointment Preparations of All Racemic 15-Deoxy-16-Hydroxy-16-Vinyl-PGE$_2$ and the Methyl Ester Thereof on the Mean Arterial Blood Pressure of Spontaneously Hypertensive Rats Experimental protocol was the same as that described in Example 1, except that the following ointment preparation of approximately 0.95% by W/W of all racemic 15-deoxy-16-hydroxy-16-vinyl-PGE$_2$ and the methyl ester thereof was employed:

| Prostaglandin Formulation | %W/W | Control Formulation % W/W |
| --- | --- | --- |
| White Petrolatum, USP | 79.24 | 80.00 |
| Diisopropyl Adipate | 19.81 | 20.00 |
| Prostaglandin | .95 | — |

Approximately 25 mg (range 20–30 mg) of the preparation was applied.

Figure 2:
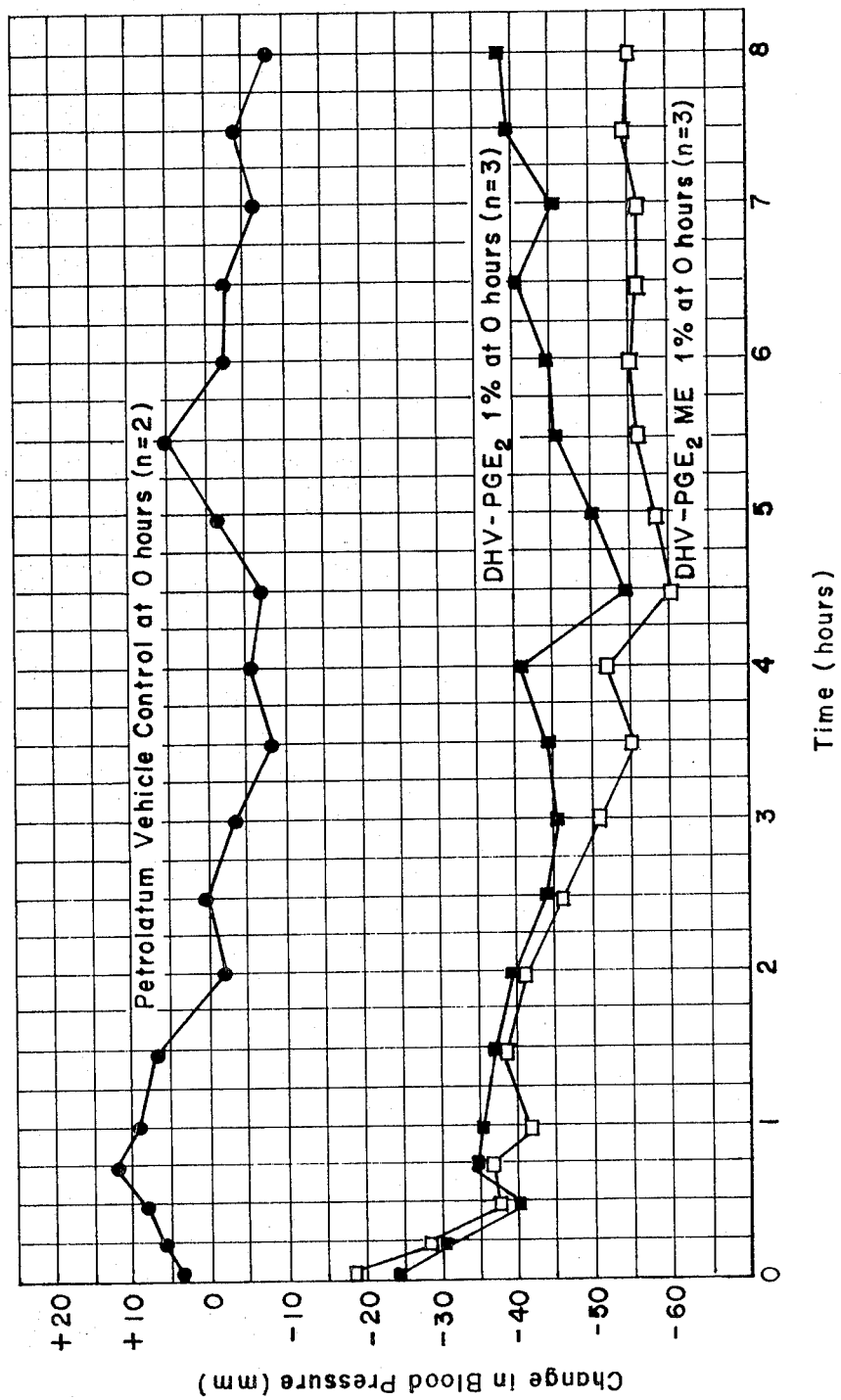

The effects of the ointment formulation of 15-deoxy-16-hydroxy-16-vinyl-PGE$_2$ and the methyl ester thereof on the mean arterial blood pressure of spontaneously hypertensive rats recorded over an 8-hour period is summarized in FIG. 2. The control and prostaglandin formulations were administered at 0 hours and the reference n refers to the number of rats tested.

Topical formulations may also be prepared containing epinephrine or other vasoconstrictors or vasodilators which increase or decrease the rate of drug absorption to control the rate of onset of hypotensive activity.

EXAMPLE 3

Effect of Drug Delivery System Topical Application of 15-Deoxy-16-Hydroxy-16-Vinyl-PGE$_2$ and Related Prostaglandins on the Mean Arterial Blood Pressure of Spontaneously Hypertensive Rats For drug delivery system administration, 1% and 3% solutions by W/W of the active prostaglandin in the following solvents listed in Table II may be prepared. Solutions may also be prepared employing the solvents listed in Table I and the E$_1$ series compound corresponding to the E$_2$ series compound listed in Table I. A drug delivery bandage containing the active prostaglandin solution and capable of administering an effective dosage of the prostaglandin may be applied to the depilated abdomen of a spontaneously hypertensive rat. The prostaglandin can be encapsulated by conventional techniques in a sustained release polymeric material. A polymeric system for continuous administration by absorption includes hydrophilic polymers such as 2-hydroxyethyl methacrylate crosslinked with ethylene glycol dimethacrylate. Prostaglandin containing microcapsules can be used with dermatologically acceptable pressure-sensitive adhesives which permit drug migration. Such adhesives include acrylic resins, such as polymers of acrylic acids and their esters. The microcapsules of prostaglandin and pressure-sensitive adhesive are applied on a backing material such as cellophane to produce a bandage which effectively provides for continuous administration through the skin to circulation.

The mean arterial blood pressure of the rat may be monitored as described in Example 1. An average decrease in the mean arterial blood pressure may result from the foregoing procedure.

TABLE I

Benzyl alcohol and 15-deoxy-16-hydroxy-16-vinyl-PGE$_2$

Amyl alcohol and 15-deoxy-16-hydroxy-16-vinyl-PGE$_2$ 1,2-Butanediol and 15-deoxy-16-hydroxy-16-vinyl-PGE$_2$ Glycerol and 15-deoxy-16-hydroxy-16-vinyl-PGE$_2$ Heptyl Aldehyde and 15-deoxy-16-hydroxy-16-vinyl-PGE$_2$ Cyclohexanone and 15-deoxy-16-hydroxy-16-vinyl-PGE$_2$ Limonene and 15-deoxy-16-hydroxy-16-vinyl-PGE$_2$ Thymol and 15-deoxy-16-hydroxy-16-vinyl-PGE$_2$ n-Hexylchloride and 15-deoxy-16-hydroxy-16-vinyl-PGE$_2$ Qermin Oil and 15-deoxy-16-hydroxy-16-vinyl-PGE$_2$ n-Hexylbromide and 15-deoxy-16-vinyl-PGE$_2$ Benzyl alcohol and 15-deoxy-16-hydroxy-16-vinyl-PGE$_2$ methyl ester Amyl alcohol and 15-deoxy-16-hydroxy-16-vinyl-PGE$_2$ methyl ester 1,2-Butanediol and 15-deoxy-16-hydroxy-16-vinyl-PGE$_2$ methyl ester Glycerol and 15-deoxy-16-hydroxy-16-vinyl-PGE$_2$ methyl ester Heptyl Aldehyde and 15-deoxy-16-hydroxy-16-vinyl-PGE$_2$ methyl ester Cyclohexanone and 15-deoxy-16-hydroxy-16-vinyl-PGE$_2$ methyl ester Limonene and 15-deoxy-16-hydroxy-16-vinyl-PGE$_2$ methyl ester Thymol and 15-deoxy-16-hydroxy-16-vinyl-PGE$_2$ methyl ester n-Hexylchloride and 15-deoxy-16-hydroxy-16-vinyl-PGE$_2$ methyl ester n-Hexylbromide and 15-deoxy-16-hydroxy-16-vinyl-PGE$_2$ methyl ester Quermin oil and 15-deoxy-16-hydroxy-16-vinyl-PGE$_2$ Benzyl alcohol and 15-deoxy-16-hydroxy-16-vinyl-20-methyl-PGE$_2$ Amyl alcohol and 15-deoxy-16-hydroxy-16-vinyl-20-methyl-PGE$_2$ 1,2-Butanediol and 15-deoxy-16-hydroxy-16-vinyl-20-methyl-PGE$_2$ Glycerol and 15-deoxy-16-hydroxy-16-vinyl-20-methyl-PGE$_2$ Heptyl Aldehyde and 15-deoxy-16-hydroxy-16-vinyl-20-methyl-PGE$_2$ Cyclohexanone and 15-deoxy-16-hydroxy-16-vinyl-20-methyl-PGE$_2$ Limonene and 15-deoxy-16-hydroxy-16-vinyl-20-methyl-PGE$_2$ Thymol and 15-deoxy-16-hydroxy-16-vinyl-20-methyl-PGE$_2$ n-Hexylchloride and 15-deoxy-16-hydroxy-16-vinyl-20-methyl-PGE$_2$ Benzyl alcohol and 15-deoxy-16-hydroxy-16-cyclopropyl-PGE$_2$ Amyl alcohol and 15-deoxy-16-hydroxy-16-cyclopropyl-PGE$_2$ 1,2-Butanediol and 15-deoxy-16-hydroxy-16-cyclopropyl-PGE$_2$ Glycerol and 15-deoxy-16-hydroxy-16-cyclopropyl-PGE$_2$ Heptyl Aldehyde and 15-deoxy-16-hydroxy-16-cyclopropyl-PGE$_2$ Cyclohexanone and 15-deoxy-16-hydroxy-16-cyclopropyl-PGE$_2$ Limonene and 15-deoxy-16-hydroxy-16-cyclopropyl-PGE$_2$ Thymol and 15-deoxy-16-hydroxy-16-cyclopropyl-PGE$_2$ n-Hexylchloride and 15-deoxy-16-hydroxy-16-cyclopropyl-PGE$_2$ n-Hexylbromide and 15-deoxy-16-hydroxy-16-cyclopropyl-PGE$_2$ Qermin Oil and 15-deoxy-16-hydroxy-16-chloropropyl-PGE$_2$ Glycerol and 15-deoxy-16-hydroxy-16-methyl-PGE$_2$ or its methyl ester Benzyl alcohol and 15-deoxy-16-hydroxy-16-methyl-PGE$_2$ methyl ester Amyl alcohol and 15-deoxy-16-hydroxy-16-methyl-PGE$_2$ methyl ester 1,2-Butanediol and 15-deoxy-16-hydroxy-16-methyl-PGE$_2$ methyl ester Heptyl Aldehyde and 15-deoxy-16-hydroxy-16-methyl-PGE$_2$ or its methyl ester Benzyl alcohol and 15-deoxy-16-hydroxy-PGE$_2$ or its methyl ester Amyl alcohol and 15-deoxy-16-hydroxy-PGE$_2$ or its methyl ester 1,2-Butanediol and 15-deoxy-16-hydroxy-PGE$_2$ or its methyl ester Glycerol and 15-deoxy-16-hydroxy-PGE$_2$ or its methyl ester Cyclohexanone and 15-deoxy-16-hydroxy-16-methyl-PGE$_2$ or its methyl ester Limonene and 15-deoxy-16-hydroxy-16-methyl-PGE$_2$ or its methyl ester Thymol and 15-deoxy-16-hydroxy-16-methyl-PGE$_2$ or its methyl ester n-Hexylchloride and 15-deoxy-16-hydroxy-16-methyl-PGE$_2$ or its methyl ester n-Hexylchloride and 15-deoxy-16-hydroxy-16-methyl-PGE$_2$ or its methyl ester Quermin Oil and 15-deoxy-16-hydroxy-16-methyl-PGE$_2$ or its methyl ester Heptyl Aldehyde and 15-deoxy-16-hydroxy-PGE$_2$ or its methyl ester Cyclohexanone and 15-deoxy-16-hydroxy-PGE$_2$ or its methyl ester Limonene and 15-deoxy-16-hydroxy-PGE$_2$ or its methyl ester Thymol and 15-deoxy-16-hydroxy-PGE$_2$ or its methyl ester n-Hexylchloride and 15-deoxy-16-hydroxy-PGE$_2$ or its methyl ester n-Hexylbromide and 15-deoxy-16-hydroxy-PGE$_2$ or its methyl ester Quermin Oil and 15-deoxy-16-hydroxy-PGE$_2$ or its methyl ester Benzyl alcohol and 15-deoxy-16-hydroxy-16-vinyl-PGE$_1$ or its methyl ester Amyl alcohol and 15-deoxy-16-hydroxy-16-vinyl-PGE$_1$ or its methyl ester 1,2-Butanediol and 15-deoxy-16-hydroxy-16-vinyl-PGE$_1$ or its methyl ester Glycerol and 15-deoxy-16-hydroxy-16-vinyl-PGE$_1$ or its methyl ester Heptyl Aldehyde and 15-deoxy-16-hydroxy-16-vinyl-PGE$_1$ or its methyl ester Cyclohexanone and 15-deoxy-16-hydroxy-16-vinyl-PGE$_1$ or its methyl ester Limonene and 15-deoxy-16-hydroxy-16-vinyl-PGE$_1$ or its methyl ester Thymol and 15-deoxy-16-hydroxy-16-vinyl-PGE$_1$ or its methyl ester n-Hexylchloride and 15-deoxy-16-hydroxy-16-vinyl-PGE$_1$ or its methyl ester n-Hexylbromide and 15-deoxy-16-hydroxy-16-vinyl-PGE$_1$ or its methyl ester Quermin Oil and 15-deoxy-16-hydroxy-16-vinyl-PGE$_1$ or its methyl ester Benzyl alcohol and 15-deoxy-16-hydroxy-16-ethynyl-PGE$_1$ or its methyl ester Amyl alcohol and 15-deoxy-16-hydroxy-16-ethynyl-PGE$_1$ or its methyl ester Thymol and 15-deoxy-16-hydroxy-16-ethynyl-PGE$_1$ or its methyl ester n-Hexylchloride and 15-deoxy-16-hydroxy-16-ethynyl-PGE$_1$ or its methyl ester n-Hexylbromide and 15-deoxy-16-hydroxy-16-ethynyl-PGE$_1$ or its methyl ester Quermin Oil and 15-deoxy-16-hydroxy-16-ethynyl-PGE$_1$ or its methyl ester 1,2-Butanediol and 15-deoxy-16-hydroxy-16-ethynyl-PGE$_1$ or its methyl ester Glycerol and 15-deoxy-16-hydroxy-16-ethynyl-PGE$_1$ or its methyl ester Heptyl Aldehyde and 15-deoxy-16-hydroxy-16-ethynyl-PGE$_1$ or its methyl ester Cyclohexanone and 15-deoxy-16-hydroxy-16-ethynyl-PGE$_1$ or its methyl ester Limonene and 15-deoxy-16-hydroxy-16-ethynyl-PGE$_1$ or its methyl ester Benzyl alcohol and 15-deoxy-16-hydroxy-16-ethynyl-PGE$_2$ or its methyl ester Amyl alcohol and 15-deoxy-16-hydroxy-16-ethynyl-PGE$_2$ or its methyl ester 1,2-Butanediol and 15-deoxy-16-hydroxy-16-ethynyl-PGE$_2$ or its methyl ester Glycerol and 15-deoxy-16-hydroxy-16-ethynyl-PGE$_2$ or its methyl ester Heptyl alcohol and 15-deoxy-16-hydroxy-16-ethynyl-PGE$_2$ or its methyl ester Cyclohexanone and 15-deoxy-16-hydroxy-16-ethynyl-PGE$_2$ or its methyl ester Limonene and 15-deoxy-16-hydroxy-16-ethynyl-PGE$_2$ or its methyl ester Thymol and 15-deoxy-16-hydroxy-16-ethynyl-PGE$_2$ or its methyl ester n-Hexylchloride and 15-deoxy-16-hydroxy-16-ethynyl-PGE$_2$ or its methyl ester n-Hexylbromide and 15-deoxy-16-hydroxy-16-ethynyl-PGE$_2$ or its methyl ester Zuermin Oil and 15-deoxy-16-hydroxy-16-ethynyl-PGE$_2$ or its methyl ester

EXAMPLE 4

Effects of Topically Applied All Racemic 15-deoxy-16-hydroxy-16-vinyl-PGE$_2$ on Guinea Pig Skin Male albino guinea pigs, weighing 250 to 400 g were shaved and depilated on their flanks, the evening before testing, with a standard mixture of barium sulfide and gum acacia. On the day of testing all racemic 15-deoxy-16-hydroxy-16-vinyl-PGE$_2$ was dissolved at a concentration of 10 mg/ml in either DMSO or ethanol. Tenfold dilutions (1 mg/ml) of each were also prepared. Vehicle controls were DMSO or ethanol alone. A 0.5 ml aliquot of the 10 mg/ml ethanol solution was mixed with 0.5 g of Aquatain ® base yielding preparations of 5 mg/g by W/W of the prostaglandin. Vehicle control was prepared by mixing 0.5 ml of ethanol in 0.5 g Aquatain ® base.

Three 2.5 cm diameter circles were drawn with a black marking pen on the flank of each guinea pig. Vehicle was applied to one of the circles and one (or two) concentrations of drug to the other circle by means of a cotton applicator stick (one swab). The amount of material deposited to the entire area within the circle(s) was estimated by weighing the applicator stick after immersion in drug or vehicle and again after swabbing the guinea pig skin. Average amounts deposited were 11 mg (range 9–13 mg) for the ethanol and DMSO preparations, and 24 mg (range 18–31 mg) for the Aquatain ® preparations.

Each circle was graded at 1, 2 and 24 hours after application of compound or vehicle according to the following:

0—no erythema
0.5—incomplete circle of faint erythema
1.0—complete circle of distinct erythema
2.0—intense erythema The effect of 15-deoxy-16-hydroxy-16-vinyl-PGE$_2$ on guinea pig skin is summarized in Table II.

TABLE II

| Treatment | 1 hour | | | 2 hours | | | 24 hours | | |
|---|---|---|---|---|---|---|---|---|---|
| | A | B | C | A | B | C | A | B | C |
| A = 15-deoxy-16-hydroxy-16-vinyl-PGE$_2$ 10 mg/ml DMSO<br>B = 15-deoxy-16-hydroxy-16-vinyl-PGE$_2$ 1 mg/ml DMSO<br>C = DMSO | 0.6 | 0.4 | 0 | 0.9 | 0.5 | 0 | 0.4 | 0 | 0 |
| A = 15-deoxy-16-hydroxy-16-vinyl-PGE$_2$ 10 mg/ml ETOH<br>B = 15-deoxy-16-hydroxy-16-vinyl-PGE$_2$ 1 mg/ml ETOH<br>C = ETOH | 0.8 | 0 | 0 | 0.4 | 0 | 0 | 0.5 | 0 | 0 |
| A = 15-deoxy-16-hydroxy-16-vinyl-PGE$_2$ 5 mg/g Aquatain ®<br>B = Aquatain ®<br>C = 15-deoxy-16-hydroxy-16-vinyl-PGE$_2$ 5 mg/g Aquatain ® | 1.5 | 0 | 1.5 | 1.5 | 0 | 1.5 | 0.5 | 0 | 0.3 |

EXAMPLE 5

Comparative Effects of Topically Applied All Racemic 15-deoxy-16-hydroxy-16-vinyl-PGE$_2$ and Related Prostaglandins on Guinea Pig Skin Male albino guinea pigs were prepared for testing as described in Example 4. The compounds tested were dissolved in ethanol at concentrations of 10 mg/ml, and 0.5 ml of this solution mixed with 0.5 g of Aquatain ® base. Two 3.5 cm diameter circles were drawn with a black marking pen on the flank of each guinea pig. 15-Deoxy-16-hydroxy-16-vinyl-PGE$_2$ was applied to the entire area within one circle and a second prostaglandin was applied to the area within the other circle. Two guinea pigs were used for each comparison. Each circle was then graded for erythema at 1, 2 and 24 hours after application of compound. The results are summarized in Table III and the names of the compounds A–P tested are listed in Table IV.

TABLE III

Comparative Effects of Topically Applied All 15-deoxy-16-hydroxy-16-vinyl-PGE$_2$ and Related Compounds on Guinea Pig Skin

| Compound | Number of Guinea Pigs | Average Score[a] of Compound A/Compound B-W | | |
|---|---|---|---|---|
| | | 1 hour | 2 hours | 24 hours[d] |
| B | 2 | 2/.8 | 2/1 | 1.5/.8 |
| C | 2 | 2/1 | 2/1 | 1.5/.8 |
| D | 2 | 1.5/.5 | 2/.5 | 2/.8 |
| E | 2 | 2/1 | 2/.8 | 1.5/.8 |
| F | 9 | 1.7/1.7 | 1.8/1.8 | 1.2/1.0 |
| G | 2 | 2/1 | 2/1.5 | 1.5/.5 |
| H | 2 | 1.5/.5 | 1.5/.8 | 1.5/0 |
| I | 2 | 1.5/.8 | 2/.8 | 1.5/.5 |
| J | 2 | 2/1 | 2/1 | 1.5/.8 |
| K | 2 | 1/.5 | 2/.8 | 1/.5 |
| L | 2 | 2/.8 | 2/.8 | 1.5/.3 |
| M | 2 | 1.5/.8 | 2/.8 | .8/.5 |
| N | 2 | 2/.8 | 2/.8 | 1/.3 |
| O | 2 | 2/1 | 2/.8 | 1/.5 |
| P | 2 | 2/.8 | 2/.8 | 1.5/.5 |
| Ethanol | 2 | 2/.5 | 2/.3 | 1.5/.3 |

[a]Scoring system: 0—no erythema; 0.5—incomplete circle or faint erythema; 1.0—complete circle of distant erythema; 2,0—intense erythema.
[b]All compounds were applied as 0.5% preparations in a 1:1 Aquatain ® in ethanol solution.
[d]At 24 hours, most areas of application appear darkened rather than erythematous and scoring at this time reflects primarily darkness of area.

TABLE IV

Tested Compounds A-P

A. 9-oxo-11α,16-dihydroxy-16-vinyl-5cis,13,-trans prostadienoic acid
B. 1-PGE$_2$
C. 15-deoxy-16-hydroxy-PGE$_2$ methyl ester
D. 15-deoxy-16-hydroxy-16-methyl-17-trans-PGE$_2$
E. 15-deoxy-16-hydroxy-16-methyl-PGE$_2$
F. 15-deoxy-16-hydroxy-16vinyl-PGE$_2$ methyl ester
G. 1,9-dioxo-1-hydroxymethyl-11α,16-dihydroxy-16-vinyl-13-trans-prostene
H. 9-oxo-11α,16-dihydroxy-16-vinyl-20-nor-5-cis,13-trans-prostadienoic acid
I. 1,9-dioxo-1-hydroxymethyl-11α,16-dihydroxy-16-vinyl-5-cis, 13-trans-prostadiene
J. 9-oxo-11α,16-dihydroxy-16-ethynyl-5-cis,13-trans-prostadienoic acid
K. 1,9-dioxo-1-hydroxymethyl-11α,16-dihydroxy-16-ethyl-5cis, 13-trans-prostadiene.
L. 9-oxo-11α,16-dihydroxy-16-vinyl-20-ethyl-5-cis,13-trans-prostadienoic acid
M. 9-oxo-11α,16-dihydroxy-16-cyclopropyl-5-cis,13-trans-prostadienoic acid
N. 9-oxo-11α,16-dihydroxy-16-vinyl-20-methyl-5-cis,13-trans-prostadienoic acid
O. 9-oxo-11α,16-dihydroxy-16-(2-propenyl)-5-cis,13-trans-prostadienoic acid
P. 9-oxo-11α,16-dihydroxy-13-trans,17-trans-prostadienoic acid

EXAMPLE 6

Effect of Topically Applied All Racemic 15-deoxy-16-hydroxy-16-vinyl-PGE$_2$ on Monkey Skin A female rhesus monkey (6.2 kg) was lightly anesthetized with 1 ml of Ketalar. ® Two adjacent rectangular areas of approximately 2 cm×3 cm on each forearm, abdomen and thigh were shaved. All racemic 15-deoxy-16-hydroxy-16-vinyl-PGE$_2$ in ethanol (10 mg/ml or 1 mg/ml) or ethanol alone was applied to each of the shaved areas of skin by means of a cotton applicator stick. Each entire area was swabbed twice, depositing approximately 0.030–0.060 ml of the solution. Each area was graded immediately after swabbing (time 0), and at 30, 60, 152, 270, 390 minutes for the degree of erythema according to the following:

0—no erythema
0.5—faint erythema
1.0—distinct erythema
2.0—intense erythema

Just prior to each of these readings an additional 0.5 ml of Ketalar ® was administered. The results are summarized in Table V.

TABLE V

Effect of Topically Applied All Racemic 15-deoxy-16-hydroxy 16-vinyl-PGE$_2$ on Rhesus Monkey Skin

| Spot[e] | Concentration[a] | Timed Score[c] After Treatment (Minutes) | | | | | | |
|---|---|---|---|---|---|---|---|---|
| | | 0 | 10 | 30 | 60 | 150 | 270 | 390 |
| A Prostaglandin[d] | 10 mg/ml in ETOH | 0 | 0 | 0 | 0.5 | 1.0 | 0.5 | 0 |
| B ETOH | | 0 | 0 | 0 | 0.5 | 0.5 | 0.5 | 0 |
| C Prostaglandin[d] | 1 mg/ml in ETOH | 0 | 0.5 | 0.5 | 0.5 | 0.5 | 0 | 0 |
| D ETOH | | 0 | 0 | 0 | 0 | 0 | 0 | 0 |
| E Prostaglandin[d] | 10 mg/ml in ETOH | 0 | 0.5 | 0.5 | 0.5 | 0.5 | 0.5 | 0.5 |
| F ETOH | | 0 | 0 | 0 | 0 | 0 | 0 | 0 |
| G Prostaglandin[d] | 1 mg/ml in ETOH | 0 | 1.0 | 1.0 | 1.0 | 1.0 | 1.0 | 0.5[b] |
| H ETOH | | 0 | 0 | 0 | 0 | 0 | 0 | 0 |
| I Prostaglandin[d] | 10 mg/ml in ETOH | 0 | 0.5 | 1.0 | 1.0 | 2.0 | 2.0 | 2.0[b] |
| J ETOH | | 0 | 0 | 0 | 0 | 0 | 0 | 0 |

[a]Amount of solution applied approximately 25–50 μl of 15-deoxy-16-hydroxy-16-vinyl-PGE$_2$ solution in stated solvent and at stated concentration.
[b]Increase in area size.
[c]Scoring: 0—no erythema, 0.5—faint erythema, 1.0—distinct erythema, 2.0—intense erythema.
[d]15-deoxy-16-hydroxy-16-vinyl-PGE$_2$.
[e]The spot positions are forearm, thigh and abdomen.

EXAMPLE 7

Effect of Concentration of 15-deoxy-16-hydroxy-16-vinyl-PGE$_2$ ETOH/Aquatain ® on Intensity of Erythema Produced on Guinea Pig Skin Male albino guinea pigs were prepared for testing as described in Example 4 above. A 0.1 ml aliquot of one of several ethanol solutions of 15-deoxy-16-hydroxy-16-vinyl-PGE$_2$, i.e., 50, 25, 20, 10 and 5 mg/ml was mixed with 0.9 gm of Aquatain. ®

Figure 3:
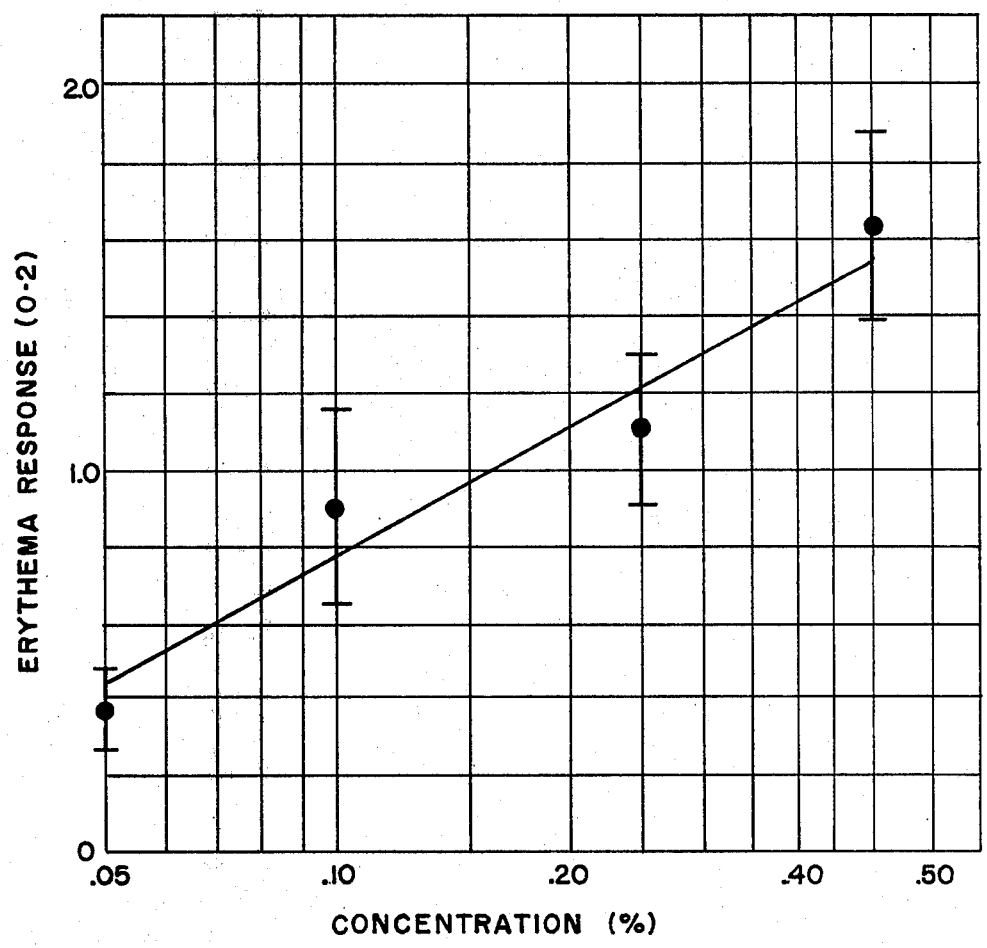

Two 3.5 cm circles were drawn on both flanks of each of six guinea pigs. Three of four concentrations of 15-deoxy-16-hydroxy-16-vinyl-PGE$_2$ in ETOH-/Aquatain ® were applied to separate circles and vehicle alone to the fourth. The absolute and relative positions of the different concentrations were varied. Each circle was graded for erythema at 2 hours after application on a 0-2 basis as described in Example 4. Control scores were subtracted from treatment scores, and these corrected values then plotted against log concentration using linear regression analysis in FIG. 3.

EXAMPLE 8

Effect of Topically Applied All Racemic 15-deoxy-16-hydroxy-16-vinyl-PGE$_2$ or the Methyl Ester thereof on Rabbit Ear Skin Temperature The dorsal ear surfaces of rabbits weighing approximately 4 kg were shaved. 15-Deoxy-16-hydroxy-16-vinyl-PGE$_2$ or the methyl ester thereof (approximately 80–100 μl of a 5 mg/ml ethanol solution) was applied to the entire dorsal surface of one ear and an equal volume of ethanol as a control was applied to the entire dorsal surface of the other ear.

Figure 4:
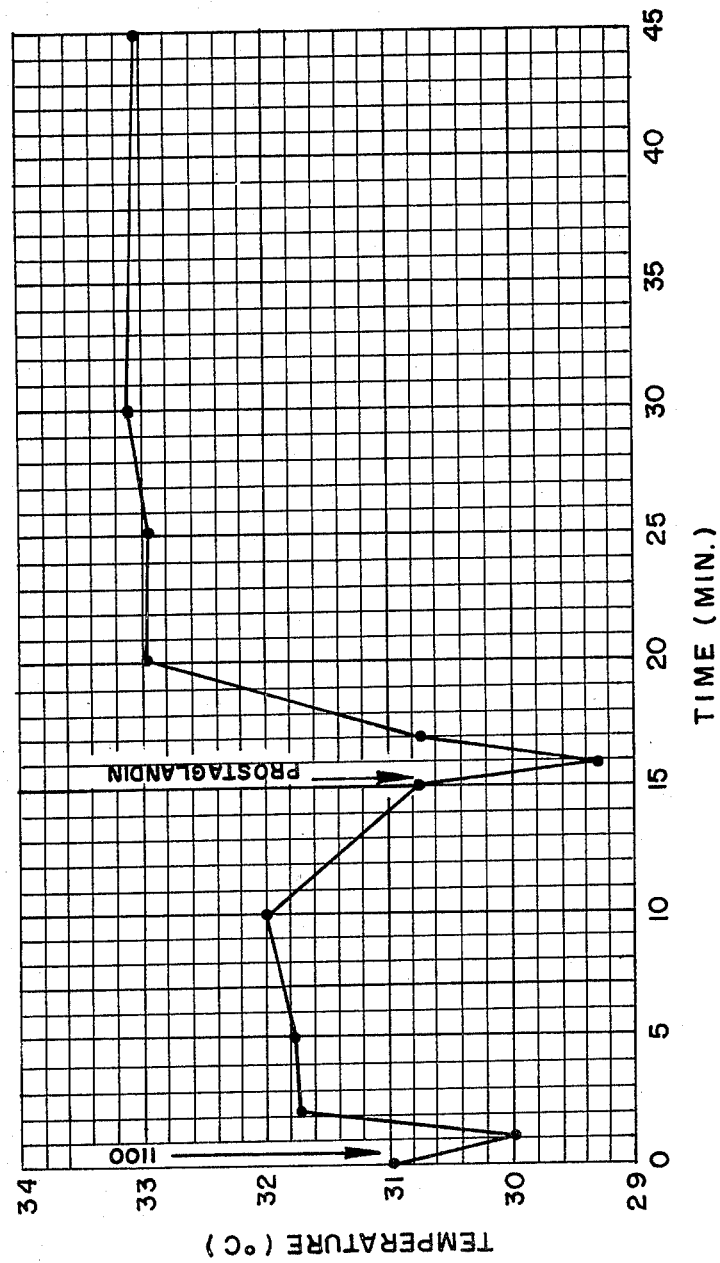
Figure 5:
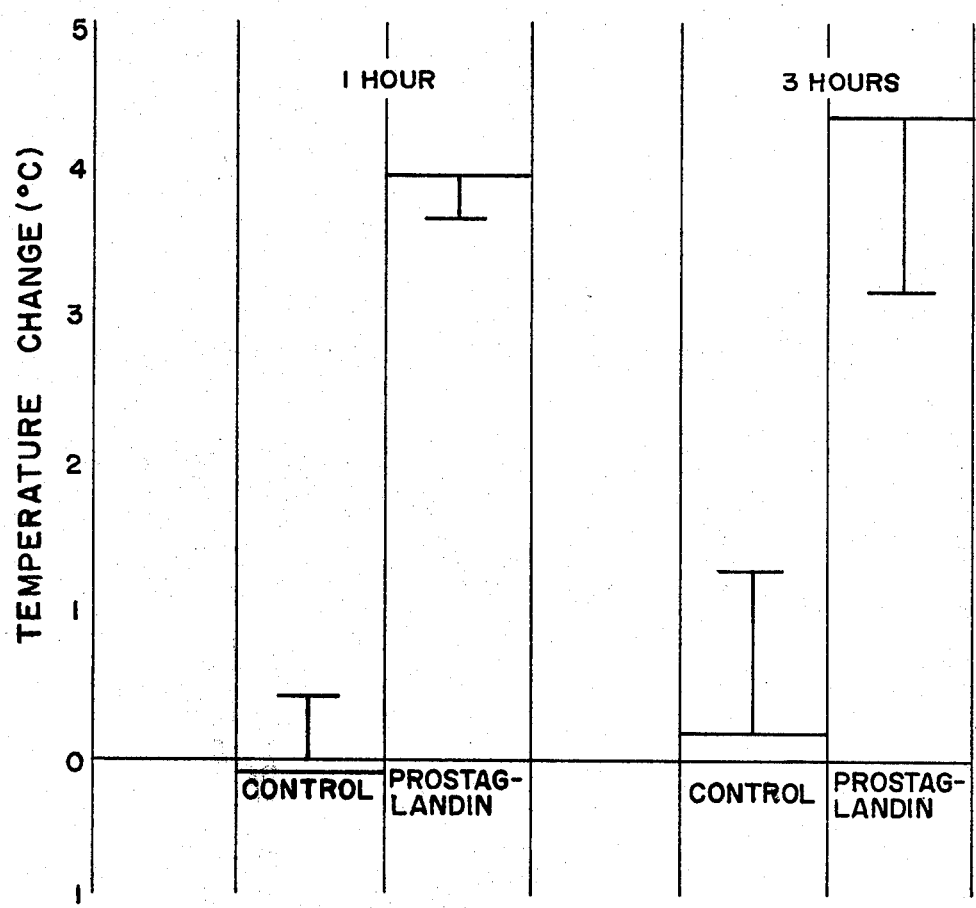

Skin temperatures were recorded on a Digital Thermistor thermometer (Digitec Model 5810) by means of a 709A surface probe. The probe was attached with a metal clip to the edge of the dorsal ear surface. In one experiment (FIG. 4) the temperature was monitored continuously from the same position on one ear, treated sequentially with ethanol and 15-deoxy-16-hydroxy-16-vinyl-PGE$_2$, 5 mg/ml in ethanol. In a second experiment (FIG. 4) the probe was shifted at specified times between corresponding positions on ethanol or protaglandin (5mg/ml in ethanol) treated ears of the same rabbit. In experiments described in FIG. 5, skin temperatures were recorded before and 1 and 3 hours after application. Mean temperature changes (before vs. after) produced by the prostaglandin solution or ethanol control are presented in FIG. 3 along with the standard error of the mean. Statistical comparison of means by Student's Test indicates that the temperature effects of the prostaglandin compared to those of the control are significant at $P<0.05$. The results of these experiments are summarized in FIGS. 4 and 5 below, wherein temperature is assumed to be a reflection of vasodilation and blood flow.

EXAMPLE 9

(Topical Formulations)

The following topical formulations employing the prostaglandins of the natural and synthetic analogs of the PGE, PGA and PGF$_\beta$ types can produce an increase in peripheral blood flow in the area of administration.

| Prostaglandin (mg) | Ethanol (ml) | Aquatain ® (gm) |
|---|---|---|
| 2.5 | 0.5 | 0.5 |
| 2.5 | 0.1 | 0.9 |
| 2.5 | 0.005 | 0.95 |
| 2.5 | — | 1.0 |
| 2.5 | 1.0 | — |
| 5.0 | 0.1 | 0.9 |
| 5.0 | 1.0 | — |
| 5.0 | — | 1.0 |
| 1.0 | 0.1 | 0.9 |
| 1.0 | — | 1.0 |
| 1.0 | 1.0 | — |
| 0.5 | 0.1 | 0.9 |
| 0.5 | 1.0 | — |
| 0.5 | — | 1.0 |

| CREAM | |
|---|---|
| Prostaglandin | 0.25 gm |
| Spermacen | 2.7 gm |
| Beeswax | 2.7 gm |
| Carbapol 934 q.s. | 100.0 gm |

-continued

| CREAM | |
|---|---|
| Prostaglandin | 0.25 gm |
| Polyethylene glycol 400 | 37.5 gm |
| 1,2,6-hexanetriol | 20.0 gm |
| Polyethylene glycol 4000 q.s. | 100 gm |

| CREAM | |
|---|---|
| Prostaglandin | 0.25 gm |
| Polyethylene glycol 400 | 37.0 gm |
| Polyethylene glycol 400 monostearate | 26.0 gm |
| Polyethylene glycol 4000 q.s. | 100.0 gm |

| CREAM | |
|---|---|
| Prostaglandin | 0.25 gm |
| Polyethylene glycol 400 | 47.5 gm |
| Cetyl Alcohol | 5.0 gm |
| Polyethylene glycol 4000 q.s. | 100.0 gm |

| OINTMENT | |
|---|---|
| Prostaglandin | 0.25 gm |
| Anhydrous lanolin | 20.0 gm |
| Mineral Oil | 25.0 gm |
| White Petrolatum q.s. | 100.0 gm |

| CREAM (Acquatain ®) | % W/W |
|---|---|
| Benzyl alcohol | 2.2% |
| Ethoxylated Stearyl Alcohol (Polywax) | 12.5% |
| Isopropyl Palmitate | 2.0% |
| Glycerin | 4.0% |
| Sorbitol Solution | 5.0% |
| Purified Water | 74.1951 |
| Prostaglandin | .161 |

| OINTMENT | |
|---|---|
| White Petrolatum, USP | 79.80 gm |
| Diisopropyl Adipate | 19.95 gm |
| Prostaglandin | .25 gm |

In addition to the above-listed topical formulation components, antioxidants such as mixed tocopherols may be added in the range of about 0.01% to 0.5% by W/W. Viscosity modifies may also be added, such as paraffin wax, lanolin wax or other compatable solid waxes. Epinephrine or other compounds which increase the rate of absorbtion of the prostaglandin may also be added to the formulations.

EXAMPLE 10

Topical formulations of 15-deoxy-16-hydroxy-16-vinyl-PGE$_2$ or its methyl ester thereof are prepared containing the following ingredients:

| Ingredients | % W/W | Approximate Range |
|---|---|---|
| White Petrolatum, USP | 79.00 gm | 75 to 95% |
| Diisopropyl Adipate | 20.00 gm | 5 to 25% |
| Prostaglandin | 1.00 gm | .01 to 2% |
| White Petrolatum, USP | 79.00 gm | 75 to 95% |
| Polyethylene Glycol 200 Dioleate | 20.00 gm | 5 to 25% |
| Prostaglandin | 1.00 gm | .01 to 2% |

In addition to the above ingredients, antioxidants such as mixed tocopherols may be added in the range of from about 0.01% to 0.5% by W/W. Viscosity modifiers such as paraffin wax, lanolin wax or other compatable waxes may also be added to the formulations. The formulations described above may also be prepared employing in place of petrolatum, an anhydrous vehicle comprising mineral oil and high molecular weight polyethylene waxes, i.e., Plastibase ®.

The formulations of this Example may be applied topically to produce an increase in peripheral blood flow in the area of administration.

EXAMPLE 11

Lotion Formulation 100 gm of a topical lotion is prepared from the following types and amounts of ingredients:

| Prostaglandin | 1.25 gm |
|---|---|
| Propylene glycol q.s. | 500 ml |

This composition is applied topically to the skin to enhance local blood flow.

EXAMPLE 12

Topical Hypotensive Formulations

For hypotensive application topical formulations containing the ingredients listed in the formulations of Examples 9-11 are prepared containing from 0.5 to 20% by W/W of the prostaglandin, the weight percentages of the other ingredients of the formulations of Examples 9 and 10 may be decreased proportionately.

EXAMPLE 13

Cream formulation for Topical Hypotensive Applications of 15-Deoxy-16-Hydroxy-16-Vinyl-PGE$_2$ or the Methyl Ester Thereof Cream preparations of the above prostaglandins for hypotensive administration are prepared containing the following ingredients:

| Ingredients | % W/W |
|---|---|
| Aquatain ® | 99.5-80 |
| Prostaglandin | 0.5-20 |
| Aquatain ® | 99.5-95 |
| Prostaglandin | 0.5-5 |

The aquatain may also be employed as a 10% ethanol or other alcohol in Aquatain ® solution.

EXAMPLE 14

Ointment Formulations For Topical Hypotensive Applications of 15-Deoxy-16-Hydroxy-16-Vinyl-PGE$_2$ or the Methyl Ester Thereof Ointment formulations of the above cited prostaglandins are prepared containing the following ingredients:

| Ingredients | % W/W |
|---|---|
| White Petrolatum, USP | 75 to 95% |
| Diisopropyl Adipate or Polyethylene Glycol 200 Dioleate | 5 to 25% |
| Prostaglandin | 5 to 20% |

| Ingredients | % W/W |
|---|---|
| White Petrolatum, USP | 79.24 |
| Diisopropyl Adipate | 19.81 |
| Prostaglandin | .95 |

EXAMPLE 15

Prostaglandin Anti-Hypertensive Oral Capsule Formulation

Oral capsule formulations containing the active prostaglandin are prepared containing the following ingredients:

| Ingredients | % W/w | Range |
|---|---|---|
| Glyceryl Triacetate FCC | gs ad 100 ml | — |
| Prostaglandin | 0.020 gm | .005 to .2% |

The dosage of 15-deoxy-16-hydroxy-16-vinyl-$PGE_2$ or its methyl ester in this formulation and employing a 0.5 ml gelatin capsule may be 100 mcg/capsule. This formulation may also be prepared using sesame oil, USP in place of the glyceryl triacetate.

EXAMPLE 16

Injectable Formulations

A sterile aqueous solution for injection containing in 1 cc. 10 mg of the prostaglandins of the instant invention is prepared from the following types and amounts of materials:

| Prostaglandin | 10 gm |
|---|---|
| Lidocaine hydrochloride | 4 gm |
| Methylparaben | 2.5 gm |
| Propylparaben | 0.17 gm |
| Water for injection q.s. | 1000 cc |

The ingredients are dissolved in the water and the solution sterilized by filtration. The sterile solution is filled into vials and the vials sealed. The composition is to be used immdiately.

EXAMPLE 17

A sterile aqueous solution for injection containing in 1 cc 1 mg of the prostaglandins of the instant invention, as the Na salt is prepared from the following types and amounts of ingredients:

| Prostaglandin | 1 gm |
|---|---|
| Sodium chloride 10% solution q.s. | |
| Water for injection q.s. | 1000 cc |

EXAMPLE 18

Preparation of Injectable Formulations

Parenteral grade prostaglandin is dissolved in anhydrous N,N-dimethylacetamide containing 0.4% water (determined by the Karl Fischer Method) in the proportions of 5 mg of the prostaglandin for each ml of anhydrous N,N-dimethylacetamide. The solution is then filter sterilized by passing it through a microporous (solvent-resistant) filter, e.g., Millipore Solvinert, 0.25 microns or Gelman Metricel Alpha-8, 0,2 microns, aseptically packaged in 1 ml quantities in sterile ampuls and kept under refrigeration at not more than 5° until needed. At that time the contents of one ampul (1 ml) are diluted into 1 liter of infusion solution and administered by high pressure injection, intradermally for the treatment of peripheral vascular disorders of the arteriospastic and occlusive types.

EXAMPLE 19

The formulations of Examples 9–11 and 16–18 are applied locally either topically or by injection to an ischemic area of the skin for the treatment of peripheral vascular disorders of the occlusive or arteriospastic types.

EXAMPLE 20

The injectable formulations of Examples 16–18 may also be employed for anti-hypertensive applications when administered in single or multiple doses by injection of about 25 mg to 2500 mg per kg of body weight total per day. The concentration of the prostaglandin in the vehicle may be increased or decreased to adjust the total amount of the formulation administered by injection.

EXAMPLE 21

The compositions of Examples 9–11 and 16–18 can similarly be employed to treat Raynaud's phenomenon, Raynaud's disease, Buergers disease, livedo, reticularis acrocyanosis, atherosclerosis, frostbite, vitiligo, alopecia areata, psoriasis, atopic dermatitis, acne and impending gangrene.

EXAMPLE 22

Additional prostaglandins for use in this invention, and for formulation with a pharmaceutical carrier are listed below in Table VII. These may be formulated and applied topically in the manner discussed above, particularly in a pharmaceutical carrier cream or in a sustained drug delivery system.

TABLE 8

11-deoxy-16-p-fluorophenoxy-17,20-tetranor $PGE_2$ and esters
11-deoxy-16,20-methano $PGE_1$ and esters
11-deoxy-16,20-methano $PGE_2$ and esters
11-deoxy-16,19-methano-20-nor-$PGE_1$ and esters
11-deoxy-16,19-methano-20-nor-$PGE_2$ and esters
16-fluoro $PGE_1$ and esters
11,15-bisdeoxy-16-hydroxy-17-methyl $PGE_1$
11-deoxy-16,16-trimethylene-17-phenyl-18,20-trinor-$PGE_1$ and esters
11-deoxy-16,16-trimethylene-17-phenyl-18,20-trinor-$PGE_2$ and esters
11-deoxy-16-p-chlorophenoxy-17,20-tetranor $PGE_1$ and esters
11-deoxy-16-p-chlorophenoxy-17,20-tetranor $PGE_2$ and esters
11-deoxy-16-p-fluorophenoxy-17,20-tetranor $PGE_1$ and esters
15(S)-15-methyl $PGE_2$ and esters
15(R)-15-methyl $PGE_2$ and esters
15(S)-15-methyl $PGE_1$ and esters
15(R)-15-methyl $PGE_1$ and esters
16,16-dimethyl $PGE_1$ and esters
16,16-dimethyl $PGE_2$ and esters
16,16-trimethylene $PGE_1$ and esters
16,16-trimethylene $PGE_2$ and esters
16,16-trimethylene-18-yne $PGE_1$ and esters
16,16-trimethylene-cis-18-ene-$PGE_1$ and esters
16,16-trimethylene-18-yne $PGE_2$ and esters
16,16-trimethylene-cis-18-ene $PGE_2$ and esters
16,16-trimethylene-17-phenyl-18,20-trinor-$PGE_1$ and esters 16,16-trimethylene-17-phenyl-18,20-trinor-PGE$_2$ and esters
16-methyl PGE$_1$ and esters
16-methyl PGE$_2$ and esters
16-methylene PGE$_1$ and esters
16-methylene PGE$_2$ and esters
erythro 16-hydroxy PGE$_1$ and esters
erythro 16-hydroxy PGE$_2$ and esters
threo 16-hydroxy PGE$_1$ and esters
threo 16-hydroxy PGE$_2$ and esters
erythro 16-hydroxy-trans-17-ene PGE$_1$ and esters
erythro 16-hydroxy-trans-17-ene-PGE$_2$ and esters
erythro 16-methoxy PGE$_1$ and esters
threo 16-methoxy PGE$_1$ and esters
threo 16-methoxy PGE$_2$ and esters
16,16-difluoro PGE$_1$ and esters
16,16-difluoro PGE$_2$ and esters
16-fluoro PGE$_2$ and esters
16-phenyl-17,20-tetranor PGE$_1$ and esters
16-phenyl-17,20-tetranor PGE$_2$ and esters
17-phenyl-18,20-trinor PGE$_1$ and esters
17-phenyl-18,20-trinor PGE$_2$ and esters
16-phenoxy-17,20-tetranor PGE$_1$ and esters
16-phenoxy-17,20-tetranor PGE$_2$ and esters
16-m-trifluoromethyl phenoxy 17,20-tetranor PGE$_1$ and esters
16-m-trifluoromethyl phenoxy 17,20-tetranor PGE$_2$ and esters
16-p-chlorophenoxy-17,20-tetranor PGE$_1$ and esters
16-p-chlorophenoxy-17,20-tetranor PGE$_2$ and esters
16-p-fluorophenoxy-17,20-tetranor PGE$_1$ and esters
16-p-fluorophenoxy-17,20-tetranor PGE$_2$ and esters
16,20-methano PGE$_1$ and esters
16,20-methano PGE$_2$ and esters
16,19-methano-20-nor-PGE$_1$ and esters
16,19-methano-20-nor PGE$_2$ and esters
15-deoxy-PGE$_1$ and esters
15-deoxy-PGE$_2$ and esters
15-deoxy-16-hydroxy PGE$_1$ and esters
15-deoxy-16-hydroxy PGE$_2$ and esters
15-deoxy-16(S)-hydroxy PGE$_1$ and esters
15-deoxy-16(R)-hydroxy PGE$_1$ and esters
15-deoxy-16-hydroxy-trans-17-ene PGE$_2$ and esters
15-deoxy-16-hydroxy-16-methyl PGE$_1$ and esters
15-deoxy-16-hydroxy-16-methyl PGE$_2$ and esters
15-deoxy-16-hydroxy-16-methyl-trans-17-ene PGE$_2$ and esters
15-deoxy-16-hydroxy-16-vinyl PGE$_1$ and esters
15-deoxy-16-hydroxy-16-vinyl PGE$_2$ and esters
15-deoxy-16-hydroxy-17-methyl PGE$_2$ and esters
11,15 bisdeoxy-16-hydroxy PGE$_1$ and esters
11,15 bisdeoxy-16-hydroxy PGE$_2$ and esters
11,15 bisdeoxy-16(S)-hydroxy PGE$_1$ and esters
11,15 bisdeoxy-16(R)-hydroxy PGE$_1$ and esters
11,15 bisdeoxy-16-hydroxy-trans-17-ene PGE$_1$ and esters
11,15 bisdeoxy-16-hydroxy-trans-17-ene PGE$_2$ and esters
11,15 bisdeoxy-16-hydroxy-16-methyl PGE$_1$ and esters
11,15 bisdeoxy-16-hydroxy-16-methyl PGE$_2$ and esters
11,15 bisdeoxy-16-hydroxy-16-methyl-trans-17-ene PGE$_1$ and esters
11,15 bisdeoxy-16-hydroxy-16-methyl-trans-17-ene PGE$_2$ and esters
11,15 bisdeoxy-16-hydroxy-16-vinyl PGE$_1$ and esters
11,15 bisdeoxy-16-hydroxy-16-vinyl PGE$_2$ and esters
11,15 bisdeoxy-16-hydroxy-17-methyl PGE$_1$ and esters
11,15 bisdeoxy-16-hydroxy-17-methyl PGE$_2$ and esters
11-deoxy-15(S)-15-methyl PGE$_2$ and esters
11-deoxy-15(R)-15-methyl PGE$_2$ and esters
11-deoxy-15(S)-15-methyl PGE$_1$ and esters
11-deoxy-15(R)-15-methyl PGE$_2$ and esters
11-deoxy-16,16-dimethyl PGE$_1$ and esters
11-deoxy-16,16-dimethyl PGE$_2$ and esters
11-deoxy-16,16-trimethylene PGE$_1$ and esters
11-deoxy-16,16-trimethylene PGE$_2$ and esters
11-deoxy-16,16-trimethylene-18-yne PGE$_1$ and esters
11-deoxy-16,16-trimethylene-18-ene-PGE$_1$ and esters
11-deoxy-16,16-trimethylene-18-yne PGE$_2$ and esters
11-deoxy-16,16-trimethylene-cis-18-ene and esters
11-deoxy-16-methyl PGE$_1$ and esters
11-deoxy-16-methyl PGE$_2$ and esters
11-deoxy-16-methylene PGE$_1$ and esters
11-deoxy-16-methylene PGE$_2$ and esters
11-deoxy erythro 16-hydroxy PGE$_1$ and esters
11-deoxy erythro 16-hydroxy PGE$_2$ and esters
11-deoxy threo 16-hydroxy PGE$_1$ and esters
11-deoxy threo 16-hydroxy PGE$_2$ and esters
11-deoxy erythro 16-hydroxy-trans-17-ene PGE$_1$ and esters
11-deoxy erythro 16-hydroxy-trans-17-ene-PGE$_2$ and esters
11-deoxy erythro 16-methoxy PGE$_1$ and esters
11-deoxy erythro 16-methoxy PGE$_2$ and esters
11-deoxy threo 16-methoxy PGE$_1$ and esters
11-deoxy threo 16-methoxy PGE$_2$ and esters
11-deoxy 16,16-difluoro PGE$_1$ and esters
11-deoxy 16,16-difluoro PGE$_2$ and esters
11-deoxy 16-fluoro PGE$_1$ and esters
11-deoxy 16-fluoro PGE$_2$ and esters
11-deoxy 16-phenyl-17,20-tetranor PGE$_1$ and esters
11-deoxy 16-phenyl-17,20-tetranor PGE$_2$ and esters
11-deoxy 17-phenyl-18,20-trinor PGE$_1$ and esters
11-deoxy 17-phenyl-18,20-trinor PGE$_2$ and esters
11-deoxy-16-phenoxy-17,20-tetranor PGE$_1$ and esters
11-deoxy-16-phenoxy-17,20-tetranor PGE$_2$ and esters
11-deoxy-16-m-trifluoromethyl phenoxy 17,20-tetranor PGE$_1$ and esters
11-deoxy-16-m-trifluoromethyl phenoxy 17,20-tetranor PGE$_2$ and esters
16,16-dimethyl-$\Delta^2$-trans-PGE$_1$
prostacyclin
prostacyclin sodium salt
5$\alpha$-PGI$_1$ This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed products are considered to be within the purview and scope of this invention and the following claims.

I claim:

1. A process of reducing systemic blood pressure comprising the topical application to a warm-blood animal or human of an effective amount of an optically active prostaglandin compound, of the following formula:

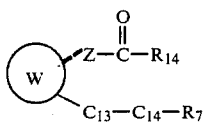

the mirror image thereof, and the racemic mixture thereof wherein W is selected from the group consisting of:

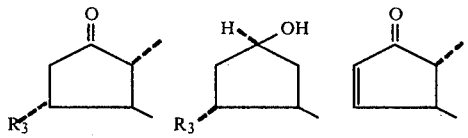

wherein $R_3$ is selected from the group consisting of hydrogen, hydroxyl and $HOCH_2CH_2S-$; Z is selected from the group consisting of $$-(CH_2)_6-, \ -CH_2-CH\overset{cis}{=}CH-(CH_2)_n-,$$
$$-(CH_2)_m-S-CH_2- \text{ and } -(CH_2)_m-O-CH_2-,$$
$$\text{and } -(CH_2)_m-O-CH_2-,$$

wherein n and m have the value of from 3 to 5 inclusive; $R_{14}$ is selected from the group consisting of hydroxyl, $C_1-C_6$ alkoxy, $-CH_2OH$ and $-CH_2OR_{15}$ wherein $R_{15}$ is $C_2-C_6$ alkanoyl; $C_{13}-C_{14}$ is ethylene or trans-vinylene; $R_7$ is a moiety selected from the group consisting of

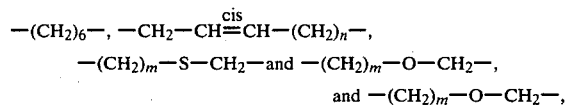

wherein $R_8$ is selected from the group consisting of

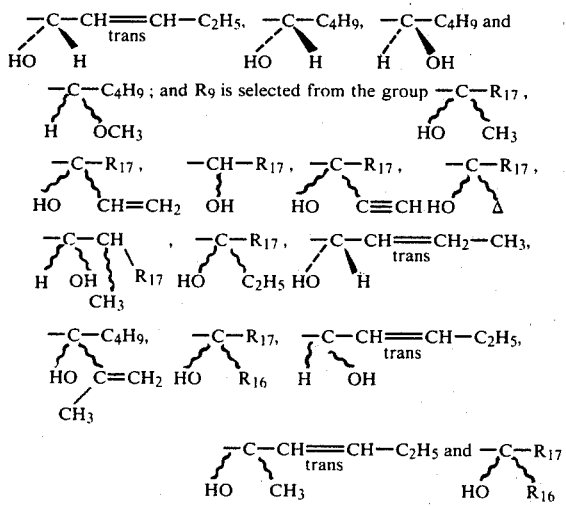

wherein $R_{16}$ is E-1-propenyl or Z-1-propenyl, $R_{17}$ is $C_3$ to $C_7$ alkyl; and, when $R_{14}$ is hydroxy, the pharmacologically acceptable cationic salts thereof.

2. The process according to claim 1, wherein n is 3 and m is 4.

3. The process according to claim 2, wherein W is

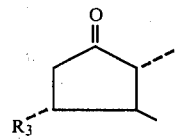

and $C_{13}-C_{14}$ is trans-vinylene.

4. The process according to claim 2, wherein W is

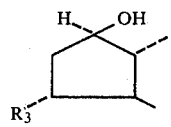

and $C_{13}-C_{14}$ is trans-vinylene.

5. The process according to claim 2, wherein W is

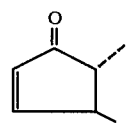

and $C_{13}-C_{14}$ is trans-vinylene.

6. The process according to claim 3, wherein $R_3$ is hydroxy.

7. The process according to claim 3, wherein Z is

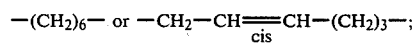

and $R_3$ is hydrogen or hydroxyl.

8. The process according to claim 1, wherein $R_7$ is selected from the group consisting of

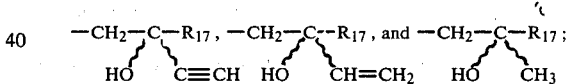

wherein $R_{17}$ is as previously defined.

9. The process according to claim 8, wherein said prostaglandin is methyl-9-oxo-11α,16-dihydroxy-16-vinyl-5-cis, 13-trans-prostadienoate.

10. The process according to claim 8, wherein said prostaglandin is 9-oxo-11α,16-dihydroxy-16-vinyl-20-nor-5-cis,13-trans-prostadienoic acid.

11. The process according to claim 8, wherein said prostaglandin is 9-oxo-11α,16-dihydroxy-16-ethynyl-5-cis,13-trans-prostadienoic acid.

12. The process according to claim 8, wherein said prostaglandin is 9-oxo-11α,16-dihydroxy-16-vinyl-20-ethyl-5-cis,13-trans-prostadienoic acid.

13. The process according to claim 8, wherein said prostaglandin is 9-oxo-11α,16-dihydroxy-16-vinyl-20-methyl-5-cis, 13-trans-prostadienoic acid.

14. The process according to claim 8, wherein said prostaglandin is 9-oxo-11α,16-dihydroxy-16-vinyl-5-cis,13-trans-prostadienoic acid.

15. The process according to claim 8, wherein said prostaglandin is nat.-9-oxo-11α,16α-dihydroxy-16-vinyl-5-cis,13-trans-prostadienoic acid.

16. The process according to claim 8, wherein said prostaglandin is nat.-methyl 9-oxo-11α,16α-dihydroxy-16-vinyl-5-cis,13-trans-prostadienoate.

17. The process according to claim 8, wherein said prostaglandin is 9-oxo-11α,16-dihydroxy-16-vinyl-13-trans-prostenoic acid.

18. The process according to claim 8, wherein said prostaglandin is nat.-9-oxo-11α,16α-dihydroxy-16-vinyl-13-trans-prostenoic acid.

19. The process according to claim 8, wherein said prostaglandin is methyl 9-oxo-11α,16-dihydroxy-16-vinyl-13-trans-prostenoate.

20. The process according to claim 8, wherein said prostaglandin is nat.-methyl 9-oxo-11α,16α-dihydroxy-16-vinyl-13-trans-prostenoate.

21. The process according to claim 8, wherein said prostaglandin is nat.-methyl 9-oxo-11α,16α-dihydroxy-16-vinyl-20-ethyl-5-cis,13-trans-prostadienoate acid.

22. The process according to claim 8, wherein said prostaglandin is nat.-9-oxo-11α,16α-dihydroxy-16-vinyl-20-nor-5-cis,13-trans-prostadienoic acid.

23. The process according to claim 8, wherein said prostaglandin is methyl 9-oxo-11α,16-dihydroxy-16-vinyl-20-nor-5-cis,13-trans-prostadienoate.

24. The process according to claim 8, wherein said prostaglandin is nat.-methyl 9-oxo-11α,16α-dihydroxy-16-vinyl-20-nor-5-cis,13-trans-prostadienoate.

25. The process according to claim 8, wherein said prostaglandin is 9-oxo-11α,16-dihydroxy-16-vinyl-20-nor-13-trans-prostenoic acid.

26. The process according to claim 8, wherein said prostaglandin is nat.-9-oxo-11α,16α-dihydroxy-16-vinyl-20-nor-13-trans-prostenoic acid.

27. The process according to claim 8, wherein said prostglandin is methyl 9-oxo-11α,16-dihydroxy-16-vinyl-20-nor-13-trans-prostenoate.

28. The process according to claim 8, wherein said prostaglandin is nat.-methyl 9-oxo-11α,16α-dihydroxy-16-vinyl-20-nor-13-trans-prostenoate.

29. The process according to claim 8, wherein said prostaglandin is methyl 9-oxo-11α,16-dihydroxy-16-vinyl-20-ethyl-13-prostadienoate.

30. The process according to claim 8, wherein said prostaglandin is nat.-9-oxo-11α,16α-dihydroxy-16-vinyl-20-methyl-5-cis,13-trans-prostadienoic acid.

31. The process according to claim 8, wherein said prostaglandin is methyl 9-oxo-11α,16-dihydroxy-16-vinyl-20-methyl-5-cis,13-trans-prostadienoate.

32. The process according to claim 8, wherein said prostaglandin is nat.-methyl 9-oxo-11α,16α-dihydroxy-16-vinyl-2-methyl-5-cis,13-trans-prostadienoate.

33. The process according to claim 8, wherein said prostaglandin is 9-oxo-11α,16-dihydroxy-16-vinyl-20-methyl-13-trans-prostenoic acid.

34. The process according to claim 8, wherein said prostaglandin is nat.-9-oxo-11α,16α-dihydroxy-16-vinyl-20-methyl-13-trans-prostenoic acid.

35. The process according to claim 8 wherein said prostaglandin is methyl 9-oxo-11α,16-dihydroxy-16-vinyl-20-methyl-13-trans-prostenoate.

36. The process according to claim 8, wherein said prostaglandin is nat.-methyl 9-oxo-11α,16α-dihydroxy-16-vinyl-20-methyl-13-trans-prostenoate.

37. The process according to claim 8, wherein said prostaglandin is nat.-9-oxo-11α,16α-dihydroxy-16-vinyl-20-ethyl-13-trans-prostenoic acid.

38. The process according to claim 8, wherein said prostaglandin is nat.-9-oxo-11α,16α-dihydroxy-16-vinyl-20-ethyl-5-cis,13-trans-prostadienoic acid.

39. The process according to claim 8, wherein said prostaglandin is methyl 9-oxo-11α,16-dihydroxy-16-vinyl-20-ethyl-5-cis,13-trans-prostadienoate.

40. The process according to claim 8, wherein said prostaglandin is nat.-methyl 9-oxo-11α,16α-dihydroxy-16-vinyl-20-ethyl-5-cis,13-trans-prostadienoate.

41. The process according to claim 8, wherein said prostaglandin is 9-oxo-11α,16-dihydroxy-16-vinyl-20-ethyl-13-trans-prostenoic acid.

42. The process according to claim 1, wherein $R_{14}$ is selected from the group consisting of

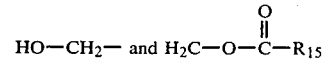

wherein $R_{15}$ is methyl or ethyl; and wherein Z is selected from the group consisting of

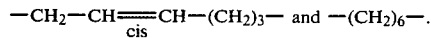

43. The process according to claim 42, wherein said prostaglandin is 1,9-dioxo-1-hydroxymethyl-11α,16-dihydroxy-16-vinyl-13-trans-prostene.

44. The process according to claim 42, wherein said prostaglandin is 1,9-dioxo-1-hydroxymethyl-11α,16-dihydroxy-16-vinyl-5-cis,13-trans-prostadiene.

45. The process according to claim 42, wherein said prostaglandin is 1,9-dioxo-1-hydroxymethyl-11α,16-dihydroxy-16-ethyl-5-cis,13-trans-prostadiene.

46. The process according to claim 42, wherein said prostaglandin is nat.-1,9-dioxo-1-hydroxymethyl-11α,16α-dihydroxy-16-vinyl-5-cis,13-trans-prostadiene.

47. The process according to claim 42, wherein said prostaglandin is 1,9-dioxo-1-hydroxymethyl-11α,16-dihydroxy-16-vinyl-20-ethyl-13-trans-prostene.

48. The process according to claim 42, wherein said prostaglandin is nat.-1,9-dioxo-1-hydroxymethyl-11α,16α-dihydroxy-16-vinyl-13-trans-prostene.

49. The process according to claim 42, wherein said prostaglandin is 1,9-dioxo-1-hydroxymethyl-11α,16-dihydroxy-16-vinyl-20-nor-5-cis,13-trans-prostadiene.

50. The process according to claim 42, wherein said prostaglandin is nat.-1,9-dioxo-1-hydroxymethyl-11α,16α-dihydroxy-16-vinyl-20-nor-5-cis,13-trans-prostadiene.

51. The process according to claim 42, wherein said prostaglandin is 1,9-dioxo-1-hydroxymethyl-11α,16-dihydroxy-16-vinyl-20-nor-13-trans-prostene.

52. The process according to claim 42, wherein said prostaglandin is nat.-1,9-dioxo-1-hydroxymethyl-11α,16α-dihydroxy-16-vinyl-20-nor-13-trans-prostene.

53. The process according to claim 42, wherein said prostaglandin is 1,9-dioxo-1-hydroxymethyl-11α,16-dihydroxy-16-vinyl-20-methyl-5-cis,13-trans-prostadiene.

54. The process according to claim 42, wherein said prostaglandin is nat.-1,9-dioxo-1-hydroxymethyl-11α,16α-dihydroxy-16-vinyl-20-methyl-5-cis,13-trans-prostadiene.

55. The process according to claim 42, wherein said prostaglandin is 1,9-dioxo-1-hydroxymethyl-11α,16-dihydroxy-16-vinyl-20-methyl-13-trans-prostene.

56. The process according to claim 42, wherein said prostaglandin is nat.-1,9-dioxo-1-hydroxymethyl-11α,16α-dihydroxy-16-vinyl-20-methyl-13-trans-prostene.

57. The process according to claim 42, wherein said prostaglandin is 1,9-dioxo-1-hydroxymethyl-11α,16-dihydroxy-16-vinyl-20-ethyl-5-cis,13-trans-prostadiene.

58. The process according to claim 42, wherein said prostaglandin is nat.-1,9-dioxo-1-hydroxymethyl-11α,16α-dihydroxy-16-vinyl-20-ethyl-5-cis,13-trans-prostadiene.

59. The process according to claim 42, wherein said prostaglandin is nat.-1,9-dioxo-1-hydroxymethyl-11α,16α-dihydroxy-16-vinyl-20-ethyl-13-trans-prostene.

60. The process according to claim 1, wherein said prostaglandin is methyl-9-oxo-11α,16-dihydroxy-5-cis,13-trans-prostadienoate.

61. The process according to claim 1, wherein said prostaglandin is 9-oxo-11α,16-dihydroxy-16-methyl-5-cis,13-trans,17-trans-prostatrienoic acid.

62. The process according to claim 1, wherein said prostaglandin is 9-oxo-11α,16-dihydroxy-16-methyl-5-cis,13-trans-prostadienoic acid.

63. The process according to claim 1, wherein said prostaglandin is 9-oxo-11α,16-dihydroxy-16-cyclopropyl-5-cis,13-trans-prostadienoic acid.

64. The process according to claim 1, wherein said prostaglandin is 9-oxo-11α,16-dihydroxy-16-(2-propenyl)-5-cis,13-trans-prostadienoic acid.

65. The process according to claim 1, wherein said prostaglandin is 9-oxo-11α,16-dihydroxy-13-trans-17-trans-prostadienoic acid.

66. The process according to claim 1, wherein the prostaglandin is contained in an ointment vehicle, wherein the prostaglandin comprises from about 0.3 to 20 weight percent of the composition.

67. The process according to claim 66, wherein the composition comprises from about 0.95% to 5% by weight prostaglandin, and from about 75% to 95% by weight vehicle, wherein the vehicle includes a solubilizer, wherein the solubilizer comprises from about 5 to 25% by weight of the composition.

68. The process according to claim 67, wherein the composition includes a prostaglandin selected from the group consisting of PGE$_1$ and PGE$_2$ prostaglandins of claim 52 having a 16-vinyl substituent.

69. The process according to claim 68, wherein the prostaglandin composition comprises about 79% by weight petrolatum, about 20% by weight diisopropyl adipate or polyethylene glycol dioleate, and about 1% prostaglandin.

70. The process according to claim 68, wherein the prostaglandin composition comprises from about 1% to 5% by weight prostaglandin in an alcohol in Aquatain ® vehicle.

71. The process according to claim 1, wherein the prostaglandin is administered by a sustained release support.

72. The process according to claim 71, wherein the support includes a hydrophilic polymer.

73. The process according to claim 1, wherein the effective dosage comprises from about 0.1 mg to 10 mg per kg body weight per day.

74. The process of reducing systemic blood pressure which comprises the topical application to a hypertensive individual of an effective amount of an optically active compound of the formula:

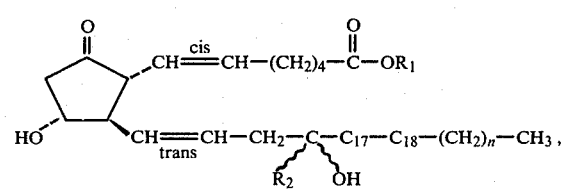

the mirror image thereof, and racemic mixtures thereof, wherein $R_1$ is selected from the group consisting of hydrogen, methyl and ethyl; $R_2$ is selected from the group consisting of hydrogen, methyl and ethyl; $C_{17}$–$C_{18}$ is selected from the group consisting of ethylene and trans-vinylene; and n is an integer from 0 to 3.

* * * * *